(12) United States Patent
Lo et al.

(10) Patent No.: US 11,253,637 B2
(45) Date of Patent: Feb. 22, 2022

(54) MULTI-CONTAINER SYSTEMS AND USES THEREOF

(71) Applicants: Richard Wai Cheong Lo, Etobicoke (CA); George Wu, Toronto (CA); Paul Yiu Wing Tam, Toronto (CA)

(72) Inventors: Richard Wai Cheong Lo, Etobicoke (CA); George Wu, Toronto (CA); Paul Yiu Wing Tam, Toronto (CA)

( * ) Notice: Subject to any disclaimer, the term of this patent is extended or adjusted under 35 U.S.C. 154(b) by 167 days.

(21) Appl. No.: 16/442,276

(22) Filed: Jun. 14, 2019

(65) Prior Publication Data

US 2019/0298905 A1    Oct. 3, 2019

Related U.S. Application Data

(63) Continuation of application No. 14/128,523, filed as application No. PCT/CA2012/000611 on Jun. 22, 2012, now Pat. No. 10,363,353.

(60) Provisional application No. 61/500,927, filed on Jun. 24, 2011.

(51) Int. Cl.
| | |
|---|---|
| *A61M 1/28* | (2006.01) |
| *A61M 1/16* | (2006.01) |
| *A61M 5/14* | (2006.01) |
| *B01D 61/24* | (2006.01) |
| *B01D 61/28* | (2006.01) |
| *A61J 1/20* | (2006.01) |

(52) U.S. Cl.
CPC .............. *A61M 1/28* (2013.01); *A61J 1/2089* (2013.01); *A61M 1/1656* (2013.01); *A61M 1/1668* (2014.02); *A61M 5/1407* (2013.01); *A61M 5/1408* (2013.01); *B01D 61/246* (2013.01); *B01D 61/28* (2013.01)

(58) Field of Classification Search
CPC ...... A61J 1/2089; A61M 1/28; A61M 5/1407; A61M 5/1408
See application file for complete search history.

(56) References Cited

U.S. PATENT DOCUMENTS

| | | |
|---|---|---|
| 4,096,859 A | 6/1978 | Agarwal et al. |
| 4,326,526 A | 4/1982 | Buck et al. |
| 4,396,382 A | 8/1983 | Goldhaber |
| 4,403,992 A | 9/1983 | Bertellini et al. |
| 4,585,436 A | 4/1986 | Davis et al. |
| 4,661,246 A | 4/1987 | Ash |
| 4,902,282 A | 2/1990 | Bellotti et al. |

(Continued)

FOREIGN PATENT DOCUMENTS

| | | |
|---|---|---|
| CA | 2201308 C | 8/2005 |
| CA | 2399440 C | 3/2007 |

(Continued)

*Primary Examiner* — Scott J Medway
(74) *Attorney, Agent, or Firm* — Venable LLP; Henry J. Daley

(57) ABSTRACT

A multi-container system apparatus comprising at least two independent containers, each container of said at least two containers for containing at least one component of the final formulation of a medium; a connector; a connecting tubing line connected to the connector; at least two output tubing lines, the first and second output tubing lines of said at least two output tubing lines connecting the first and second containers of said at least two containers, respectively, to the connecting tubing line.

22 Claims, 16 Drawing Sheets

(56) References Cited

U.S. PATENT DOCUMENTS

| | | | |
|---|---|---|---|
| 5,004,459 A | 4/1991 | Peabody et al. | |
| 5,004,548 A * | 4/1991 | Richalley | A61M 1/3643 |
| | | | 210/321.72 |
| 5,053,003 A | 10/1991 | Dadson et al. | |
| 5,531,681 A | 7/1996 | Walton et al. | |
| 5,641,405 A | 6/1997 | Keshaviah et al. | |
| 5,722,947 A | 3/1998 | Jeppsson et al. | |
| 6,491,658 B1 | 12/2002 | Miura et al. | |
| 6,919,326 B1 | 7/2005 | Miyata | |
| 6,986,872 B2 | 1/2006 | Taylor | |
| 7,011,855 B2 | 3/2006 | Martis et al. | |
| 7,053,059 B2 | 5/2006 | Zieske et al. | |
| 7,122,210 B2 | 10/2006 | Elisabettini et al. | |
| 7,169,303 B2 | 1/2007 | Sullivan et al. | |
| 7,175,606 B2 | 2/2007 | Bowman, Jr. et al. | |
| 7,198,611 B2 | 4/2007 | Connell et al. | |
| 7,208,479 B2 | 4/2007 | Naggi et al. | |
| 7,243,893 B2 | 7/2007 | Sobue et al. | |
| 7,311,886 B2 | 12/2007 | Dumont D'Ayot et al. | |
| 7,736,328 B2 | 6/2010 | Childers et al. | |
| 8,226,595 B2 | 7/2012 | Childers et al. | |
| 8,894,609 B2 | 11/2014 | Gobbi Frattini | |
| 8,992,462 B2 | 3/2015 | Childers et al. | |
| 2002/0077608 A1* | 6/2002 | Stringer | A61M 1/28 |
| | | | 604/317 |
| 2002/0120227 A1 | 8/2002 | Childers et al. | |
| 2003/0225066 A1 | 12/2003 | Polaschegg | |
| 2004/0019312 A1 | 1/2004 | Childers et al. | |
| 2004/0097862 A1 | 5/2004 | Lampeter et al. | |
| 2005/0020507 A1 | 1/2005 | Zieske et al. | |
| 2005/0209563 A1 | 9/2005 | Hopping et al. | |
| 2006/0172954 A1 | 8/2006 | Jensen et al. | |
| 2008/0125693 A1 | 5/2008 | Gavin et al. | |
| 2009/0009290 A1 | 1/2009 | Kneip et al. | |
| 2009/0012457 A1 | 1/2009 | Childers et al. | |
| 2009/0012458 A1 | 1/2009 | Childers et al. | |
| 2009/0277516 A1* | 11/2009 | Winkler | G05D 7/0635 |
| | | | 137/486 |
| 2009/0306584 A1 | 12/2009 | Schmidtlein et al. | |
| 2010/0069817 A1 | 3/2010 | Falkvall et al. | |
| 2010/0204765 A1 | 8/2010 | Hall et al. | |
| 2010/0217179 A1 | 8/2010 | Lo et al. | |
| 2011/0017665 A1 | 1/2011 | Updyke et al. | |
| 2013/0206248 A1 | 8/2013 | Brehm | |
| 2016/0101227 A1* | 4/2016 | Norris | A61M 1/3656 |
| | | | 604/29 |
| 2017/0297939 A1* | 10/2017 | Tseng | C02F 9/00 |

FOREIGN PATENT DOCUMENTS

| | | |
|---|---|---|
| CN | 101189036 A | 5/2008 |
| TW | 388717 B | 5/2000 |
| WO | 80/02706 A1 | 12/1980 |
| WO | 9508299 A1 | 3/1995 |
| WO | 9707837 A1 | 3/1997 |
| WO | 1999/003519 A1 | 1/1999 |
| WO | 0057935 A1 | 10/2000 |
| WO | 01/82996 A2 | 11/2001 |
| WO | 2006/001962 A1 | 1/2006 |
| WO | 2007/146794 A3 | 4/2008 |
| WO | 2010/096657 A1 | 8/2010 |
| WO | 2012174652 A1 | 12/2012 |

* cited by examiner

MULTI-CONTAINER SYSTEMS AND USES THEREOF

CROSS-REFERENCE TO RELATED APPLICATION

This application is a continuation of U.S. application Ser. No. 14/128,523, filed on Apr. 21, 2014, now allowed, which is a National Stage Application under 35 U.S.C. § 371 PCT/CA2012/000611, filed on Jun. 22, 2012, which claims priority benefit from U.S. Provisional Application No. 61/500,927, filed on Jun. 24, 2011, the entire content of which is incorporated herein by reference. All references cited anywhere in this specification, including the Background and Detailed Description sections, are incorporated herein by reference as if each had been individually incorporated.

FIELD OF THE INVENTION

The present invention relates to multi-container systems and uses thereof. More particularly, the present invention relates to multi-container systems for storing, mixing and/or dispensing desired media and uses thereof.

BACKGROUND OF THE INVENTION

Kidney dialysis covers both extra-corporeal (hemodialysis etc.) and intra-corporeal (peritoneal dialysis) modalities. Peritoneal dialysis is a well-established medical procedure for correcting end stage renal failure (ESRF). The principles of operation of peritoneal dialysis start with initial drain, followed by fill, dwell and drain, known as a cycle. Classification of peritoneal dialysis therapy are based on the number of cycles (fill, dwell and drain), the fill volume of dialysis fluid used per cycle, the time of treatment and whether the operation is done manually or with a machine.

Machine or automatic operations are done mostly at night using cyclers, also known as automated peritoneal dialysis (APD) machines. APD machines normally utilize 3, 5 or 15-liter pre-sterilized fluid containers (bags).

The majority of peritoneal dialysis patients are using manual peritoneal dialysis therapy, termed continuous ambulatory peritoneal dialysis (CAPD). CAPD is performed during the day and utilizes pre-sterilized 2 liters or less, fluid bags. Application of CAPD requires instillation of about two liters of prepackaged fresh sterile dialysate into the peritoneal cavity every 4 to 6 hours during 24 hours of treatment, 7 days per week.

Associated disposable peritoneal dialysis sets and the operational techniques for APD and CAPD modalities are significantly different. The sets for CAPD are very simple for manual manipulations. However, sets for APD machines are functionally complex in design and operation.

Due to the increased utilization of peritoneal dialysis for treating patients with ESRF, there is a need to provide better products to advance this medical treatment. Because of the low annual operating cost of peritoneal dialysis, coupled with initial clinical benefits, peritoneal dialysis is becoming the first choice of dialysis therapy in the developing world.

There is an urgent need to provide biocompatible peritoneal dialysis fluids and efficient techniques that could prolong the viability of the peritoneal membrane. The current art formulates media as a completed product in a single storage container. The conventional peritoneal dialysis solutions are known to be bio-incompatible because of low pH (acidic), lactate, glucose degradation products (high concentrations), and osmolality (glucose based). In addition, poor connectors, poor tubing sets and open operational systems result in frequent and/or higher peritonitis (infection) rates.

During the past decade, products have been introduced to reduce peritoneal infection rates from one episode in nine months to the current lower rate of one episode in two years or more. For example, see International Publication Nos. WO 80/02706, WO 2006/001962 and WO 2010/096657; U.S. Pat. Nos. 4,326,526, 4,902,282, 7,736,328, 7,208,479, 7,243,893, 7,311,886, 7,122,210, 7,169,303, 7,175,606, 7,198,611, 6,919,326, 6,986,872, 7,011,855, 7,053,059 and 5,053,003; and U.S. Patent Application Publication Nos. 2005/0020507, 2006/0172954, 2008/0125693 and 2010/0069817.

One of the main focuses has been on the peritoneal dialysis set itself. The major contributing products are the disinfectant caps for capping the tubing, the "Y" Set™ and the double bag system, to name a few. The "Y" Set™ includes an empty bag and connected tubes shaped like a "Y" dictating the flow of dialysis solution. Additionally, a bag filled with peritoneal dialysis solution is connected to this system. First of all, the used dialysis solution is drained into the empty bag, carrying possible bacteria from the catheter connector. Then fresh dialysis solution is flushed through the tubes and into the bag for about three seconds. The connection to the abdominal cavity remains closed during this procedure. When the tubes have been flushed, the patient's catheter connector is opened and fresh peritoneal dialysis solution is introduced into the cavity (flush-before-fill principle). Depending on the system, the flow of peritoneal dialysis solution (drainage, flush, filling) is controlled with clamps or a disc. The current double bag system uses a single container filled with dialysate and a second empty container (often of an inferior quality) used as a drain container. These products have helped to extend the effective lifetime of the peritoneal membrane and thus have prolonged peritoneal dialysis modality for the average patient. These products have also reduced the medical complications, hospitalizations and the annual treatment cost per patient. However, the search to perfect peritoneal dialysis treatment still continues. A significant number of the new dialysate packages have been targeted to CAPD patients but because CAPD is a manual operation, some of the regulatory bodies have not accepted the operational safety of the proposed new packages. Improvements to the current art teach formulation separations and/or specific partitions of dialysate. They all use different compartments in a single bag to house the separated parts that are later admixed to produce the final dialysate. For example, U.S. Pat. No. 7,243,893 relates to a compartmentalized single bag. Manufacturing processes are complex and hence the final products cost almost twice as much as the standard dialysate bags. Significantly, none of the prior art teaches any novel methods for administering additives.

Another main focus that has been, and is still undergoing extensive studies, is dialysate. It is also one of the highest costs, but essential parts, of the therapy. Dialysate may be considered as media made of multiple compositions. Commercial dialysate are formulated into a single bag, manufactured in individual container sizes, distributed and stocked until usage. However, the compounds in these commercially finished prepackaged compositions are not chemically and physically stable. It is well known in the art that some of the compounds in dialysate are catalysts that may speed up the breakdown of their companion compounds. Under certain conditions, some compounds may also induce undesirable precipitations of some of the other compounds in the dialysate. Examples of unstable compounds are glucose which undergoes caramelization and/or breakdown and bicarbonate, which precipitates. Undesirable by-products produced by caramelization of glucose (as stated previously above) during sterilization and storage; produce harmful effects on the peritoneal membrane.

In order to stabilize glucose in dialysate, hydrochloric acid, acetic acid and lactic acid are added to the solution to lower the pH of the composite dialysate (calcium, sodium, potassium, chloride etc.), to a pH of 5.3. It is known that current acidic dialysate causes infusion pain and gradually destroys the peritoneal membrane. And, even at this acidic level, glucose still undergoes caramelization during sterilization and continues to undergo gradual degradation and breakdown during storage, thus producing harmful aldehyde by-products such as, for example, formaldehyde, acetaldehyde, methylglyoxal etc. Thus, when these commercially prepared dialysate are introduced into the peritoneum of patients, these undesirable by-products and the acidity degrade the peritoneal membrane. It is relevant to note that an average peritoneal dialysis patient is infused with more than 3,000 liters of these non-biocompatible dialysis solutions per year.

Membrane damage reduces dialysis efficiency and most importantly, the length of time patients could be supported with peritoneal dialysis treatment. Patients who fail peritoneal dialysis treatment are transferred to hemodialysis. The annual cost of hemodialysis treatment may be twice as much as peritoneal dialysis. The end-stage renal disease cost containment is a major issue always at the table of the funding boards.

Clinical and animal research has identified the importance of replacing the current peritoneal dialysate with desirable alternatives that have normal pH, or higher pH near 7.2. Using current manufacturing methodologies, industries are having difficulties in re-producing desirable/beneficial dialysate that have been identified and clinically tested and proven effective over these recent years. And the selected few new dialysate that are available are priced beyond the budget of the clinics and the patients.

Thus, there is a need for a ready-to-use pre-fabricated bicarbonate dialysate, that is clinically more favorable than a glucose base solution and that is not subject to precipitation. Because of this problem desirable bicarbonate dialysate is commercially available in limited quantities and being sold at very high price.

Thus, it is an object of the present invention to overcome the deficiencies of the prior art.

Further and other objects of the invention will become apparent to those skilled in the art from reading the following summary of the invention and the preferred embodiments described and illustrated herein.

SUMMARY OF THE INVENTION

In accordance with an aspect of the present invention, there is provided a multi-container system apparatus comprising: (a) at least two supply containers capable of housing at least one substance; (b) a connector; (c) a connecting tube connected to the connector; and (d) at least two supply tubes, the first supply tube connecting the first supply container with the connecting tube and the second supply tube connecting the second supply container with the connecting tube.

In an embodiment of the present invention, at least one of the at least two supply containers comprises at least one port for the introduction and removal of the at least one substance.

In an embodiment of the present invention, the at least two supply containers are selected from the group consisting of bags, bottles, syringes, cartridges, pumps and tubing.

In an embodiment of the present invention, the apparatus comprises at least three clamps for selectively clamping any one of the supply and connecting tubes.

In an embodiment of the present invention, the at least three clamps are manually operated.

In an embodiment of the present invention, at least one of the supply and connecting tubes carries a valve.

In an embodiment of the present invention, each of the supply and connecting tubes carry a valve.

In an embodiment of the present invention, the valve is a check valve.

In an embodiment of the present invention, at least one of the supply and connecting tubes carry a locking connector.

In an embodiment of the present invention, each of the supply and connecting tubes carry a locking connector.

In an embodiment of the present invention, at least one of the supply and connecting tubes carry a filter.

In an embodiment of the present invention, each of the supply and connecting tubes carry a filter.

In an embodiment of the present invention, the filter is a micron filter.

In an embodiment of the present invention, at least one of the at least two supply containers comprises a housing diaphragm.

In an embodiment of the present invention, each of the at least two supply containers comprises a housing diaphragm.

In an embodiment of the present invention, the housing diaphragm is a breakable seal.

In an embodiment of the present invention, at least one of the supply containers contains at least one substance.

In an embodiment of the present invention, the first supply container contains at least one substance and the second supply container is empty.

In an embodiment of the present invention, the first and second supply containers contain at least one substance.

In an embodiment of the present invention, the at least one substance of the second supply container is the same as the at least one substance of the first supply container.

In an embodiment of the present invention, the at least one substance of the second supply container is different from the at least one substance of the first supply container.

In an embodiment of the present invention, the at least one substance is selected from the group consisting of a gas, a liquid, a semi-solid and a solid.

In an embodiment of the present invention, the at least one substance is in the form of a salt.

In an embodiment of the present invention, the solid is in a form selected from the group consisting of a powder, a crystal, a granule and a particle.

In an embodiment of the present invention, the at least one substance of the first supply container is at least one component of the final composition of a medium and the at least one substance of the second supply container is at least another component of the final composition of the medium.

In an embodiment of the present invention, the second supply container is configured such that the contents contained therein can flow into the first supply container to mix the contents of the second supply container with the contents of the first supply container to reconstitute a medium.

In an embodiment of the present invention, the first and second supply containers are configured such that the medium can flow back and forth at least one time between the first and second supply containers.

In an embodiment of the present invention, the first and second supply containers are configured such that the medium can flow back and forth a plurality of times between the first and second supply containers.

In an embodiment of the present invention, one of the at least two supply containers, when the contents contained therein have been transferred partially or completely out therefrom, is configured such that it can be used as a drain or a sampling container.

In an embodiment of the present invention, the second container, when the contents contained therein have been transferred partially or completely out therefrom, is configured such that it can be used as a drain or a sampling container.

In an embodiment of the present invention, the apparatus comprises three supply containers and three supply tubes, the first supply tube connecting the first supply container with the connecting tube, the second supply tube connecting the second supply container with the connecting tube, and the third supply tube for connecting the third supply container with the connecting tube.

In an embodiment of the present invention, the apparatus comprises three supply containers and three supply tubes, the first supply tube connecting the first supply container with the connecting tube, the second supply tube connecting the second supply container with the connecting tube, and third supply tube connecting the third supply container with the connecting tube.

In an embodiment of the present invention, the apparatus comprises three supply containers and three supply tubes, the first supply tube connecting the first supply container with the connecting tube, the second supply tube connecting the second supply container with the connecting tube, and third supply tube connecting the third supply container with the first supply tube.

In an embodiment of the present invention, the apparatus comprises three supply containers and three supply tubes, the first supply tube connecting the first supply container with the third supply container, the third supply tube connecting the third supply container with the connecting tube and the second supply tube connecting the second supply container with the connecting tube.

In an embodiment of the present invention, the apparatus comprises three supply containers, three supply tubes, a drain container and a drain tube, the first supply tube connecting the first supply container with the third supply container, the third supply tube connecting the third supply container with the second supply container and the second supply tube connecting the second supply container with the connecting tube, and the drain tube connecting the drain container with the connecting tube.

In an embodiment of the present invention, the apparatus comprises three supply containers, three supply tubes, a drain container and a drain tube, the first supply tube for connecting the first supply container with either the second or third supply container, the third supply tube for connecting the third supply container with the second supply container and the second supply tube connecting the second supply container with the connecting tube, and the drain tube connecting the drain container with the connecting tube.

In an embodiment of the present invention, the apparatus comprises three supply containers, three supply tubes, a drain container, and a drain tube, the first supply tube connecting the first supply container with the connecting tube, the second supply tube connecting the second supply container with the connecting tube, the third supply tube connecting the third supply container with the connecting tube, and the drain tube connecting the drain container with the connecting tube.

In an embodiment of the present invention, the apparatus comprises three supply containers and four supply tubes, the first supply tube connecting the first supply container with the connecting tube, the second supply tube connecting the second supply container with the connecting tube, the third supply tube connecting the third supply container with the connecting tube, and the fifth supply tube connecting the second supply tube with the second and third supply containers.

In an embodiment of the present invention, the apparatus comprises four supply containers and four supply tubes, the first supply tube connecting the first supply container with the connecting tube, the second supply tube connecting the second supply container with the connecting tube, and third supply tube connecting the third supply container with the first supply tube, and the fourth supply tube connecting the fourth container with the connecting tube.

In an embodiment of the present invention, the apparatus comprises four supply containers and five supply tubes, the first supply tube connecting the first supply container with the connecting tube, the second supply tube connecting the second supply container with the connecting tube, the third supply tube connecting the third supply container with the connecting tube, the fourth supply tube connecting the fourth supply container with the connecting tube, and the fifth supply tube connecting the first supply tube with the third and fourth supply containers.

In accordance with another aspect of the present invention, there is provided a multi-container system apparatus comprising: first, second and third supply containers; a connector; a connecting tube connected to the connector; first, second and third supply tubes; a drain container; and a drain tube, wherein the first, second and third supply containers are connected in series such that the first supply tube connects the first supply container with the second supply container, the second supply tube connects the second supply container with the third supply container, the third supply tube connects the third supply container with the connecting tube, and the drain tube connects the drain container with the connecting tube.

In an embodiment of the present invention, the apparatus further comprises fourth and fifth supply tubes connected with the second supply container, each of the first, second, fourth and fifth supply tubes terminating with a locking connector, wherein the second supply container is detached from the serial connection, the fourth supply tube for connecting the second supply container with the first supply tube via mating locking connectors and the fifth supply tube for connecting the second supply container with the second supply tube via mating locking connectors, the second supply tube carrying a filter between the locking connector and the third supply container, the locking connectors providing a desired option for reconnecting the second supply container in series with the first and third supply containers at any time.

In an embodiment of the present invention, the second supply container is detachable and the first supply tube communicates with the third supply container via the locking connector in line with the filter, the second supply container comprising a compatible third locking connector, the third locking connector permitting the second supply container to be inserted between the first supply container and the filter when desired and the first supply container, when emptied, may be relocated to a fourth locking connector in the fifth tubing line, to serve as a drain container or a sample container.

In an embodiment of the present invention, the third and fourth supply containers are connected in parallel with their respective supply tubes with the supply tubes of the first and second supply containers.

In an embodiment of the present invention, the supply tube of the third and/or fourth supply containers house locking connectors.

In an embodiment of the present invention, the locking connectors accommodate multiple supply containers that have compatible locking connectors.

In an embodiment of the present invention, a drain tube with a locking connector is attached to the fourth supply tube and a drain container is attached to the locking connector.

In an embodiment of the present invention, at least one of the supply containers is used as a drain container.

In an embodiment of the present invention, at least one of the supply containers is used as a sample container.

In an embodiment of the present invention, the supply tubes carry locking connectors comprising filters.

In an embodiment of the present invention, said second supply container is connected to the second supply tube via a second locking connector and another auxiliary supply container with an independent medium is attached to the port of the second supply container.

In an embodiment of the present invention, the second supply container is detachable at a second locking connector.

In an embodiment of the present invention, the second supply container that is detachable at a second locking connector comprises a filter after the second locking connector.

In an embodiment of the present invention, the second supply container is connected to the second locking connector at the start.

In an embodiment of the present invention, the second supply container has an auxiliary supply container attached to its side.

In an embodiment of the present invention, the at least one detachable second supply container comprises more than one detachable supply container which are attached in sequence to discharge their respective contents into the attached first supply container, and one of the at least one second supply containers is used as a drain container or sample container accordingly.

In an embodiment of the present invention, a third supply container is placed in the first supply tube and the third supply container houses a medium to be transferred into the first supply container, and the second supply container when emptied partially or completely, is used as a drain or a sampling container, transforming the apparatus into a double bag system.

In an embodiment of the present invention, the first supply container is connected to the first supply tube via a first locking connector that accepts different sizes of the first supply containers with same or different contents and where a filter is placed after the first locking connector.

In an embodiment of the present invention, either the first supply container or the second supply container, when their respective contents are emptied partially or completely, are utilized as the drain container of a double bag system accordingly.

In an embodiment of the present invention, the apparatus further comprises an additional two supply containers arranged in parallel with their inputs joined together and communicating with the second supply tube and the outputs of the two additional supply containers joined to the third supply tube such that the contents of the second supply container may flow through said two additional supply containers.

In an embodiment of the present invention, the first supply container and the first supply tube are removed and the contents of the second supply container could be made to flow or circulate through the two additional supply containers.

In accordance with another aspect of the present invention, there is provided a peritoneal dialysis set comprising: at least two supply containers, the first supply container of the at least two supply containers for containing at least one component of a final dialysate for filling a patient, and the second supply container of the at least two supply containers for containing at least one component of the final dialysate; a connector; a connecting tube connected to the connector; at least two supply tubes, the first supply tube of the at least two supply tubes connecting the first supply container to the connecting tube and the second supply tube of the at least two supply tubes connecting the second supply container to the connecting tube.

In an embodiment of the present invention, the connector is a junction.

In an embodiment of the present invention, the connector is a Y-junction or a T-junction.

In an embodiment of the present invention, the connector is a patient connector configured to connect to a patients' transfer set.

In an embodiment of the present invention, the peritoneal dialysis set further comprises at least three clamps, the first, second and third clamps of the at least three clamps for selectively clamping any one of the supply and connecting tubes.

In an embodiment of the present invention, the at least three clamps is manually operated.

In an embodiment of the present invention, at least one of the at least two supply containers comprises an apparatus for hanging the supply container.

In an embodiment of the present invention, each of the at least two supply containers comprise at least one port for the introduction or the removal of the at least one component of the final dialysate.

In an embodiment of the present invention, the peritoneal dialysis set further comprises a flow control device for selectively clamping any one of the supply and connecting tubes.

In an embodiment of the present invention, at least one of the at least two supply containers is a two liter container.

In an embodiment of the present invention, at least one of the supply and connecting tubes is fitted with a removable plug.

In an embodiment of the present invention, the connecting tube is sized to extend to and fit within a drain container when a patient connected to the set is sitting or standing.

In an embodiment of the present invention, one of the at least two supply containers is a drain container.

In an embodiment of the present invention, the peritoneal dialysis set further comprises at least one cap to close the connector during at least one patient dwell.

In an embodiment of the present invention, at least one of the at least two supply containers is initially full.

In an embodiment of the present invention, at least the second supply container of the at least two supply containers is filled with a different component of the final dialysate than the first supply container of the at two supply containers.

In an embodiment of the present invention, the at least two supply containers are separated by a frangible plug.

In accordance with another aspect of the present invention, there is provided a peritoneal dialysis system for use with the peritoneal dialysis set described above, the system including at least one of: (i) a drain container configured to receive and secure the connecting tube and (ii) a patient transfer set configured to connect to the connector.

In accordance with another aspect of the present invention, there is provided a peritoneal dialysis method comprising: connecting at least two supply containers to a connector, each of the first and second supply containers of the at least two supply containers full of at least one component of a final dialysate for filling a patient; transferring the at least one component of the second supply container to the first supply container to form the final dialysate; connecting the connector to a patient's transfer set; draining the patient through the connector into a drain container; and filling the patient from the first supply container.

In an embodiment of the present invention, the transfer of the at least one component of the second supply container to the first supply container is partial.

In an embodiment of the present invention, the transfer of the at least one component of the second supply container to the first supply container is complete.

In an embodiment of the present invention, connecting the at least two supply containers to the connector comprises connecting the at least two supply containers to a connecting tube connected to the connector.

In an embodiment of the present invention, connecting the connector to the patient's transfer set comprises at least one of: (i) providing a cap on the connector that is removed for connection; and (ii) configuring the connector to be connected fluidly to the patients' transfer set.

In an embodiment of the present invention, draining through the connector comprises preventing flow from the at least two supply containers to the connector, preventing flow from the first supply container to the second supply container, and urging flow from the patient to the drain container.

In an embodiment of the present invention, urging flow from the patient to the drain container comprises lowering the drain container below the patients' access point.

In an embodiment of the present invention, filling the patient from the first supply container comprises preventing flow from the connector to the second supply container, preventing flow from the first supply container to the second supply container, and urging flow from the first supply container through the connector to the patient.

In an embodiment of the present invention, the drain container is the second supply container.

In an embodiment of the present invention, urging flow from the first supply container through the connector to the patient comprises raising the first supply container above a patients' access point.

In an embodiment of the present invention, transferring the at least one component of the second supply container to the first supply container comprises preventing flow from the second supply container to the connector and urging flow from the second supply container to the first supply container.

In an embodiment of the present invention, urging flow from the second supply container to the first supply container comprises lowering the first supply container below the second supply container.

In an embodiment of the present invention, the peritoneal dialysis method further comprises flushing the supply and connecting tubes by preventing flow from the second supply container to the first supply container and urging flow from the first supply container through the supply and connecting tubes to the drain.

In an embodiment of the present invention, the peritoneal dialysis method further comprises allowing for a dialysate dwell by preventing flow from the at least two supply containers to the connector and flow from the connector to the drain.

In an embodiment of the present invention, the peritoneal dialysis method further comprises disconnecting the patients' transfer-set from the connector during the dialysate dwell.

In an embodiment of the present invention, filling a patient with a dialysate comprises filling the first supply container containing at least one component of the dialysate with at least another component of the dialysate from the second supply container to form the final dialysate and filling the patient with the final dialysate from the first supply container.

The peritoneal dialysis set of the present invention provides, in one embodiment, an improvement in the treatment of kidney dialysis patients.

The multi-container system apparatus of present invention provides, in one embodiment, the means for storing and for providing desired media (gases, liquids, semi-solids and solids including powders, crystals and granules) formulated with multiple combinations of elements, compounds and/or compositions. If these media were already formed and housed in a single container and ready for use, they may undergo transformation during sterilization, curing and/or storage. In addition, poor handling and certain environmental conditions may generate bacteria growth in the media. The containers of the present invention may be in the form of bags, bottles, syringes cartridges, pumps, tubing etc.

In the multi-container system apparatus of the present invention, components of primary media may be separated into parts and stored in one or more containers. Additives may also be housed in one or more additional containers, some of which may either be initially attached to the main system or may be in independent detachable containers that may be selectively connected to the main system via a coupling connector. The containers may be arranged in parallel or in series to achieve optimum operation and safety.

The multi-container apparatus system of the present invention also provides bi-directional fluid paths and flows to achieve easy and complete mixing of components stored in separate containers and/or compartments. The usage of the containers may be optimized in every arrangement.

Any one of the embodiments of the multi-container system apparatus of the present invention may be operated manually or with the assistance of a device, equipment and/or a machine.

In one embodiment of the present invention, the multi-container system apparatus is a peritoneal dialysis set that provides stable, safe and desirable dialysate for kidney dialysis treatments, whether this desirable dialysate is separated into parts, requires additives, undergoes sterilization or not. The apparatus of the present invention also provides a multi-container system for long-term storage of separated parts of dialysate and, later mixing the separated parts together to constitute desired final product and/or for safe addition of additives. The apparatus of the present invention further provides effective, safe and reliable applications.

Using peritoneal dialysis solution (dialysate) packaging to demonstrate the apparatus of the present invention, does not limit the scope of this invention to dialysate only or to medical applications only. Parallel applications extend to other industries as well, such as, for example, methods and procedures for mixing medications, paints, beverages, glues, solvents etc. These applications may benefit from the apparatus and method of the present invention in one or many other versions. Particularly, it is the aim of the present invention to also provide alternate and other useful embodiments that may be used individually, or in combination, to obtain unique advantages.

The novel multi-container system of the present invention provides increased reliability in the reconstitution of the final dialysate. Although the present invention benefits the CAPD technique, it is equally applicable to all forms of peritoneal modalities including manual peritoneal dialysis and the automated peritoneal dialysis systems (IPD, CCPD, NPD etc.). In general, this system would benefit any operation and/or procedure that use a singular medium or multiple media and, the medium or media, when fully constituted, may be unstable under certain processing and storage conditions.

The present invention provides an apparatus and use of an apparatus for producing and/or storing separated components of media and, later safely mixing said components to re-constitute said media for use whenever and wherever required. The components or parts of the components of the media may be reactive or non-reactive, and may be in the form of gases, liquids, solids, powders, crystals, granular and/or salts.

The embodiments of the multi-container system of the present invention may be operated manually or with an assistance of a device, equipment and/or a machine. This novel peritoneal dialysis system is being introduced to enhance the art of current CAPD/Manual procedures and to deliver varieties of acceptable biocompatible peritoneal dialysis solutions safely and at affordable prices. Also it provides the means for safely storing and for providing unaltered, desired media (gases, liquids, solids, powders, crystals, granular and/or salts) formulated with multiple combinations of compounds and/or elements. The system also teaches bidirectional material flow paths for achieving easy and complete mixing of components stored in separated but integrated containers. The usage of the containers is optimized in every arrangement to transform the system into an acceptable system equivalent to the Double Bag System™ and/or "Y" Set System™. The combinational effects of the features of the multi-container apparatus system of the present invention are to help to extend lifetime performance of peritoneal membrane. It is also based on well-proven clinical procedure that closed CAPD system, built on the principles of Double-Bag ["Y"] and "Flush-Before-Fill" operations, reduces dialysis infection rates.

The objective of the present invention is to provide a simple and reliable storage system for producing sterile biocompatible peritoneal dialysis solutions with less and/or no harmful glucose degradation end products (GDPs). This system also helps to provide near neutral pH solutions that prolong the viability of peritoneal membrane (reduce infusion pains). And for production of bicarbonate peritoneal dialysis solutions desired peritoneal dialysis solutions are separated into two or more stable parts and housed in different and independent containers for sterilization and storage until the time of usage. At the time of application the system also transforms into a closed Double Bag system for safe manual operation.

With the peritoneal dialysis set of the present invention, the osmotic agents (glucose etc.) can be stored at much lower pH, separately from the electrolytes. This reduces the formation of harmful glucose degradation products.

The peritoneal dialysis set of the present invention is optimized to provide conditions for achieving the most biocompatible peritoneal dialysis solutions: (1) higher pH (near neutral), (2) bicarbonate buffer, (3) reduced glucose degradation products, (4) osmolality (safe glucose based), (5) other alternate osmotic based peritoneal dialysis solutions (amino acids, icodextrin etc.), (6) transformation into Double Bag CAPD closed system (for reduction of infection rate).

Further and other advantages of the present invention will be understood from the rest of the specification.

BRIEF DESCRIPTION OF THE DRAWINGS

The present invention will be further understood from the following detailed description with references to the following drawings in which.

Similar references are used in different figures to denote similar components.

DETAILED DESCRIPTION OF THE PREFERRED EMBODIMENTS

Figure 1A:
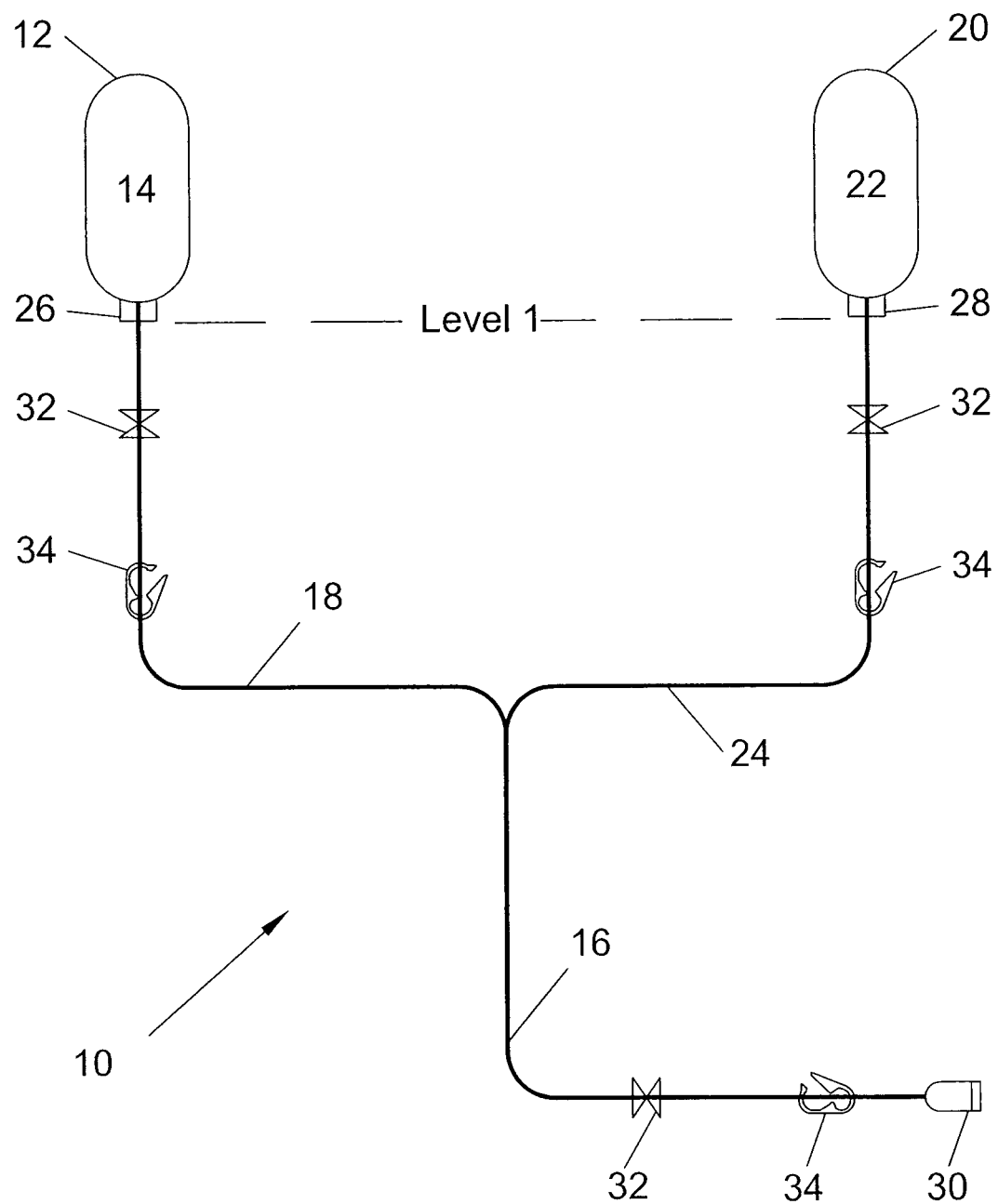
FIG. 1a illustrates one embodiment of the peritoneal dialysis set of the present invention showing two supply containers, each storing at least one component of a final dialysate and both connected to a connecting tube via their respective supply tubes.
Figure 1B:
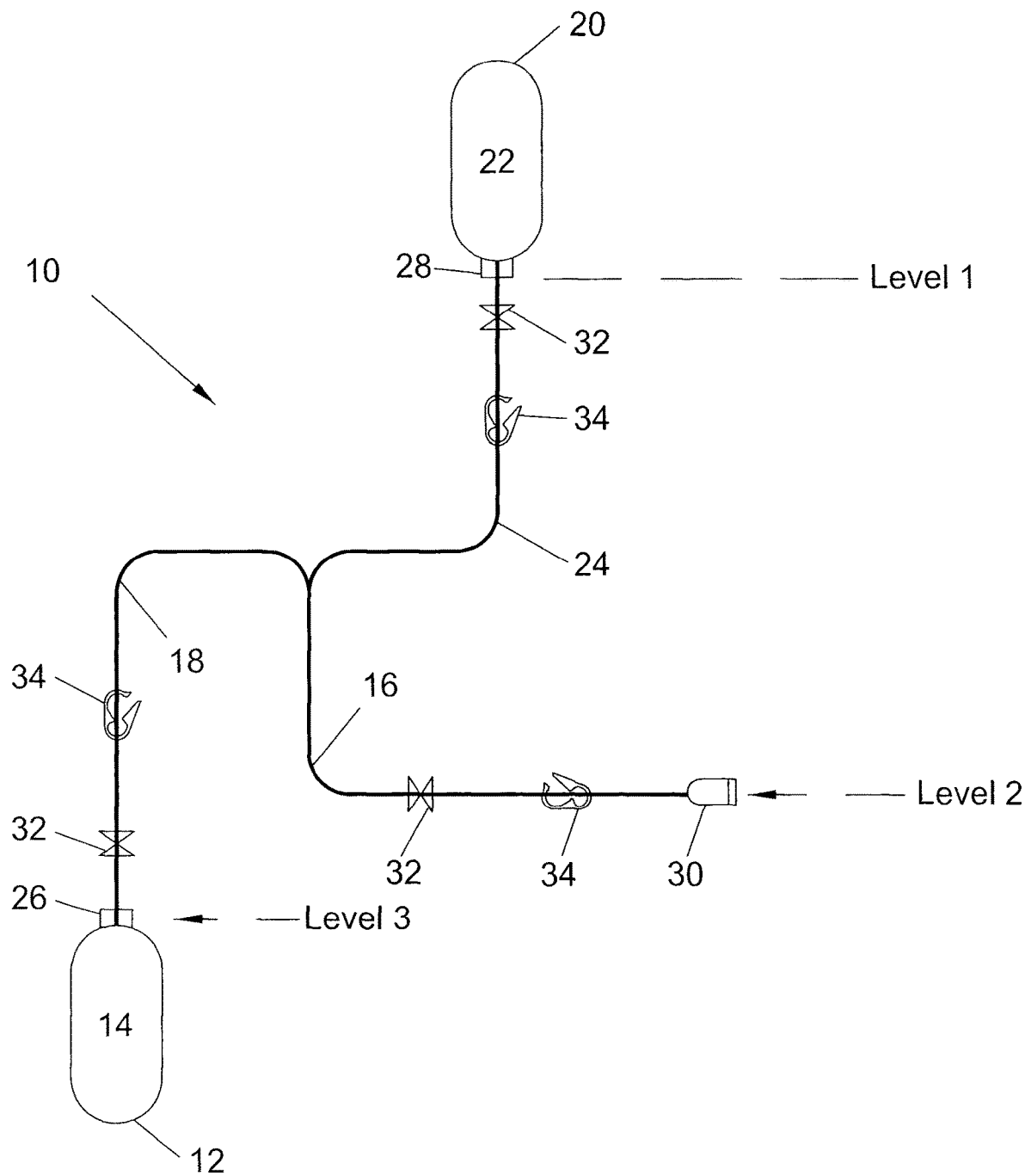
FIG. 1b illustrates the embodiment of FIG. 1a wherein the first supply container is lowered to position relative to the second supply container for performing a mixing phase using the peritoneal dialysis set of the present invention.
Figure 1C:
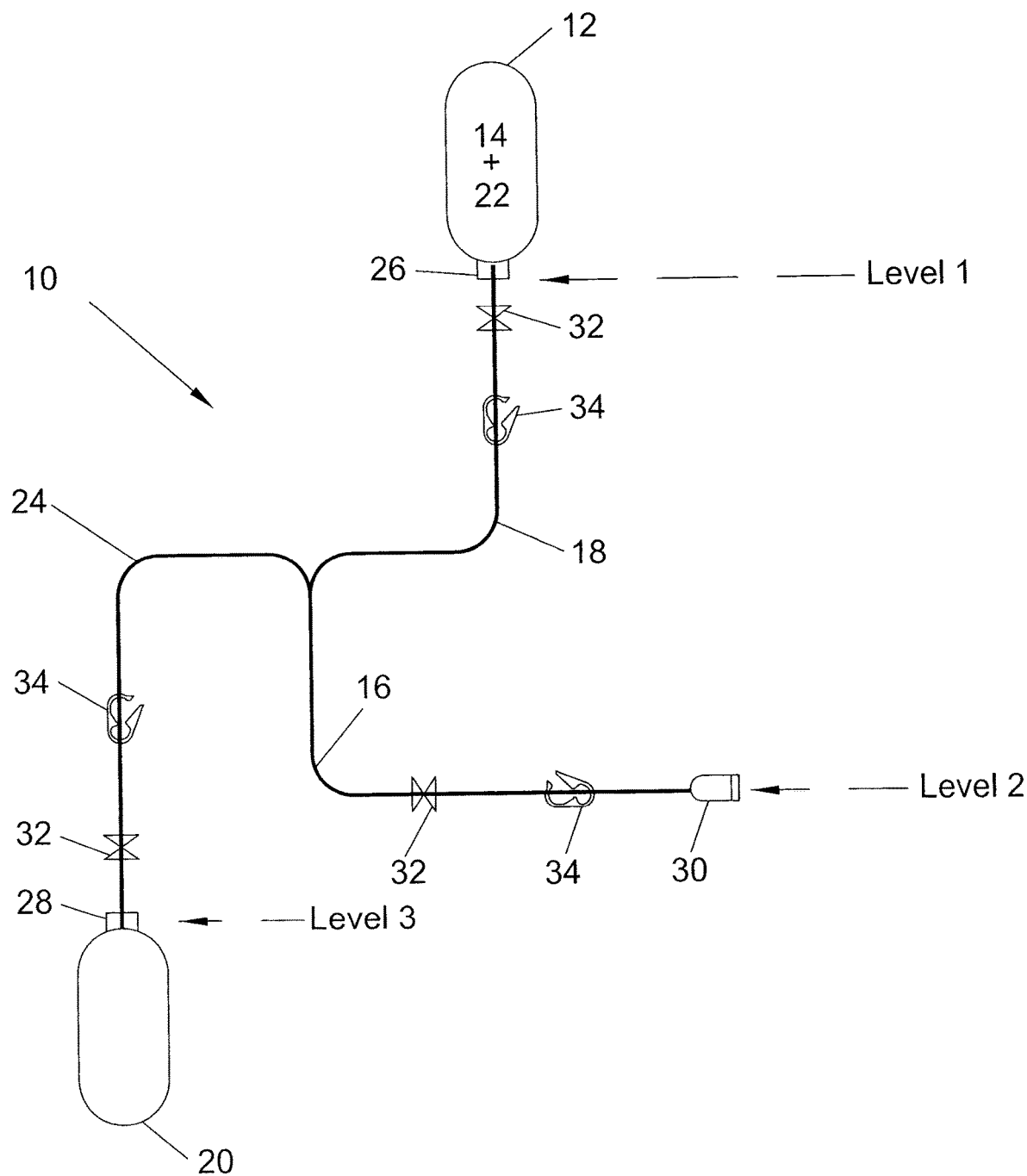
FIG. 1c illustrates the embodiment of FIGS. 1a and 1b wherein the relative positions of the first and second supply containers are exchanged for performing a drain phase followed by a filling phase.

Referring now to the drawings and in particular to FIGS. 1a, 1b and 1c, one embodiment of the multi-container system apparatus of the present invention is shown. To demonstrate an application of the apparatus of the present invention, a peritoneal dialysis double bag system is used to illustrate the administration of a normal peritoneal dialysis treatment. The peritoneal dialysis set 10 of the present invention includes a first supply container 12 containing at least one component 14 of a final dialysate for filling a patient (not shown) and fluidly connected to a connecting tube 16 via a first supply tube 18. The set 10 also includes a second supply container 20 containing at least another component 22 of the final dialysate that is fluidly connected to the connecting tube 16 via a second supply tube 24. First supply container 12 is provided with a port 26 for connecting to the connecting tube 16 via supply tube 18. Second supply container 20 is provided with port 28 for connecting to the connecting tube 16 via supply tube 24. The connecting tube 16 terminates with a patient connector 30 that is configured to mate in a releasable and fluid tight manner (e.g., threaded with o-ring seal) with a patient's transfer set (not shown), which leads to a catheter (not shown) implanted inside the patient's peritoneum (not shown). The first and second supply tubes 18 and 24 carry frangibles, in this embodiment check valves 32 that must be broken to allow flow into and out of the respective first and second supply containers 12 and 20. The first and second supply tubes 18 and 24 also carry clamps, in this embodiment reusable manual clamps 34 for controlling the flow into and out of the respective first and second supply containers 12 and 20. The connecting tube 16 also carries a frangible, in this embodiment a check valve 32 that must be broken to allow flow into and out of the patient and a clamp 34 for controlling the flow into and out of the patient. Filters (not shown), in one embodiment, micron filters, may be integrated into any supply tube or connecting tube or into any port or within any part or parts of the multi-container system apparatus of the present invention.

In one embodiment, supply containers 12 and 20, supply tubes 18 and 24, connecting tube 16 and connector 30 are made of medical grade materials, such as Class VI materials or better, e.g., PVC or polyolefin-based non-PVC material. Connector 30 can also be made of Hytrel, PVC or polycarbonate. Supply tubes 18 and 24 and connecting tube 16 can be any length. In one embodiment, supply tubes 18 and 24 can be about three feet in length and connecting tube 16 can be about 2.5 feet in length.

With the peritoneal dialysis set 10 of the present invention, supply containers 12 and 20 are both initially full and hold the patient's prescribed one cycle treatment volume (e.g., 2-3 liters) collectively in one embodiment (plus an extra amount for flushing). With the peritoneal dialysis set 10 of the present invention, the separated components 14 and 22 are used to re-generate the desired composition of the final dialysate for filling the patient. Gravitational force is used to affect the transfer of the separated components 14 and 22 and of the final dialysate throughout the entire system.

Starting with the application, the two supply containers 12 and 20 are placed at an upper altitude, level 1 (see FIG. 1a). By choice, when ready to complete the desired final formulation of the dialysate, first supply container 12 is lowered to position level 3 (see FIG. 1b). Check valves 32 of supply tubes 24 and 18, respectively are broken in sequence to open, in sequence, the supply tubes 24 and 18, respectively. Clamps 34 of supply tubes 18 and 24 respectively are then opened in sequence. By gravity, the component 22 is transferred from supply container 20 to supply container 12, where it mixes with the component 14. The resultant product (14+22) is mixed thoroughly in supply container 12 producing the final formulation of the complete dialysate for filling the patient. Then the position of supply container 12 is exchanged with the position of supply container 20, i.e., supply container 12 is moved to the higher position level 1 and the supply container 20, now empty, is moved to the lower position level 3, to become a drain container.

The patient, connected to the patient line connector 30, now drains his/her used dialysate into the second supply container 20. For safety and by practice, a small amount of the resultant product (14+22) may be drained out of supply container 12 into supply container 20 to flush the supply tubes 18 and 24 and the connecting tube 16 before filling the patient. The sterile mixed dialysate contents (14+22) in supply container 12 may now be discharged out through the patient connector 30 to the patient.

It may be acceptable to redirect the resultant product (14 and 22) back and forth between supply containers 12 and 20 more than once, if so wished, to produce efficient mixing of 14 with 22 before the final product is discharged. If preferred, the mixed product 14+22 may be stored in, and discharged from, supply container 20 rather than supply container 12. If that were the case, supply container 12 would become the empty drain container to be positioned at level 3. Then the supply container 20 would be at the highest position, level 1.

The transfer of contents from supply container into another may be achieved using gravitational force, i.e., by lowering one supply container with respect to the other. For example, when supply container 12 is placed lower than supply container 20, the medium 22 flows into supply container 12 to mix with medium 14. Persons skilled in the art knowledgeable in hydrodynamic principles would understand that media transfer, whole or partial, from one container to the others, could be achieved using other applied forces such as pressure, pumps, vacuum, centrifugal, electromagnetic, Hall Effect, screws etc. Hence, the present invention includes within its scope all applicable principles that are capable of transporting and/or transferring media, in whole or in part, from one place to another.

It may be necessary to separate the required desirable product into more than two independent components, i.e., into three or more independent components. FIGS. 2a, 2b, 2c, 3, 4a, 4b, 5a, 5b, 6a, 6b, 7 and 9 demonstrate alternate embodiments of such requirements. Some of the supply containers may not be attached to the main system to start with as shown in FIGS. 2c, 5a, 5b, 6a, 6b, 7, 8 and 9. For peritoneal dialysis, the additional container(s) may be empty or may contain at least one component of the final dialysate for filling a patient that is the same as, similar to, or different from, the at least one component contained in any of the other supply containers. The additional container(s) may contain at least one component of the final dialysate for filling a patient in an amount that is the same as, similar to, or different from, the at least one component contained in any of the other supply containers. The additional container(s) may contain at least one component of the final dialysate for filling a patient at a volume that is the same as, similar to, or different from, the at least one component contained in any of the other supply containers. For example, the additional container(s) may contain electrolytes, buffering agents and/or osmotic agents. More specifically, an additional supply container may contain either bicarbonate or dextrose concentrate to produce a final dialysate for filling a patient selected from the group consisting of a 1.5%, 2.5% and 4.25% dialysate, or other percentages of osmotic agent.

Figure 2A:
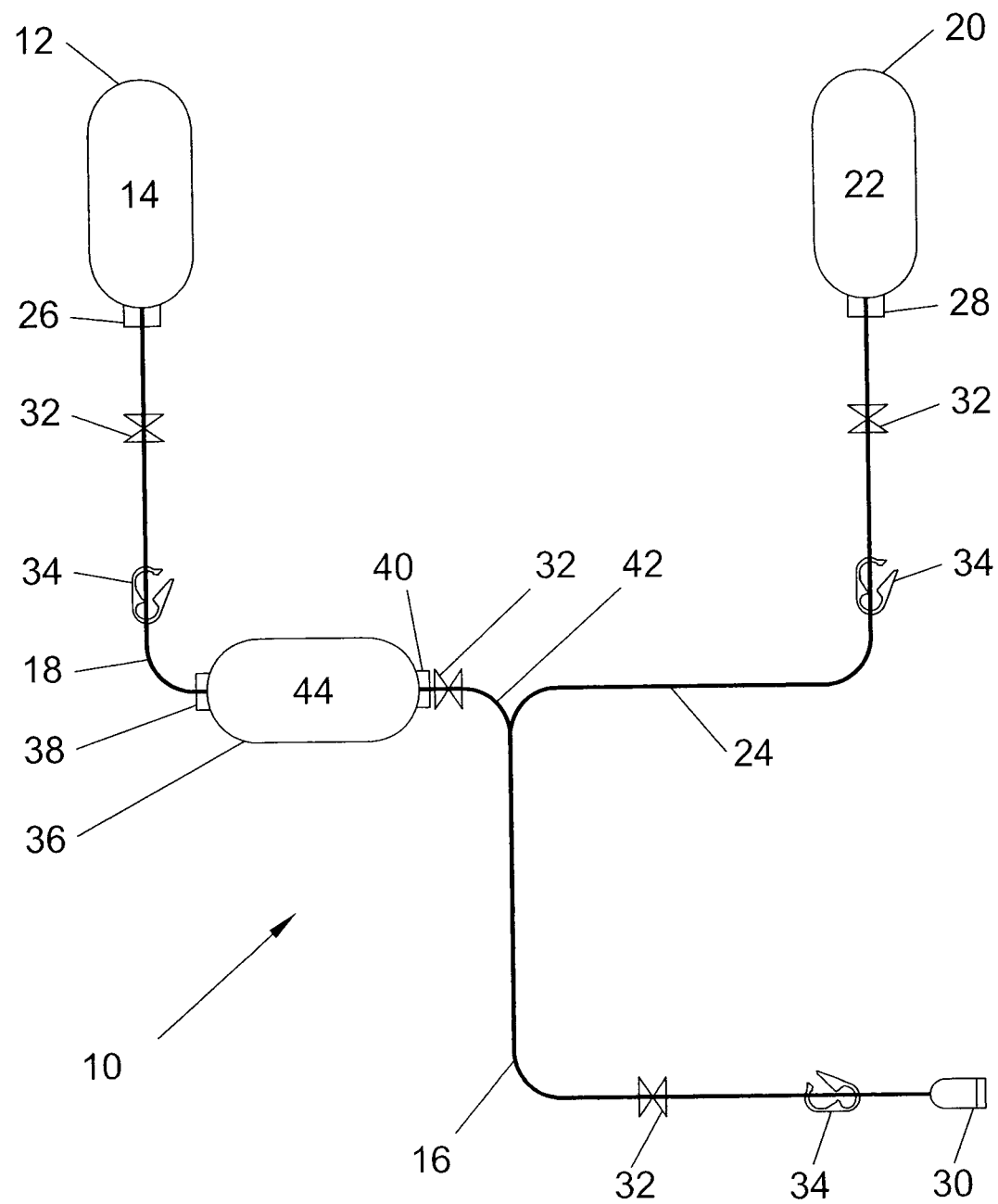
FIG. 2a illustrates another embodiment of the peritoneal dialysis set of the present invention showing three supply containers, the third supply container positioned in series with the first supply container.

FIG. 2a illustrates another embodiment of the peritoneal dialysis set 10 of the present invention wherein a third supply container 36 is arranged in series with the first supply container 12 such that the first supply container 12 is connected to the third supply container 36 through port 38 via the first supply tube 18 and the third supply container 36 is connected through port 40 to the connecting tube 16 via the third supply tube 42. Third supply container 36 may contain at least one component 44 of the final dialysate that is the same as, similar to or different from, the at least one component 14 and 22 of the first and second supply containers 12 and 20, respectively.

Figure 2B:
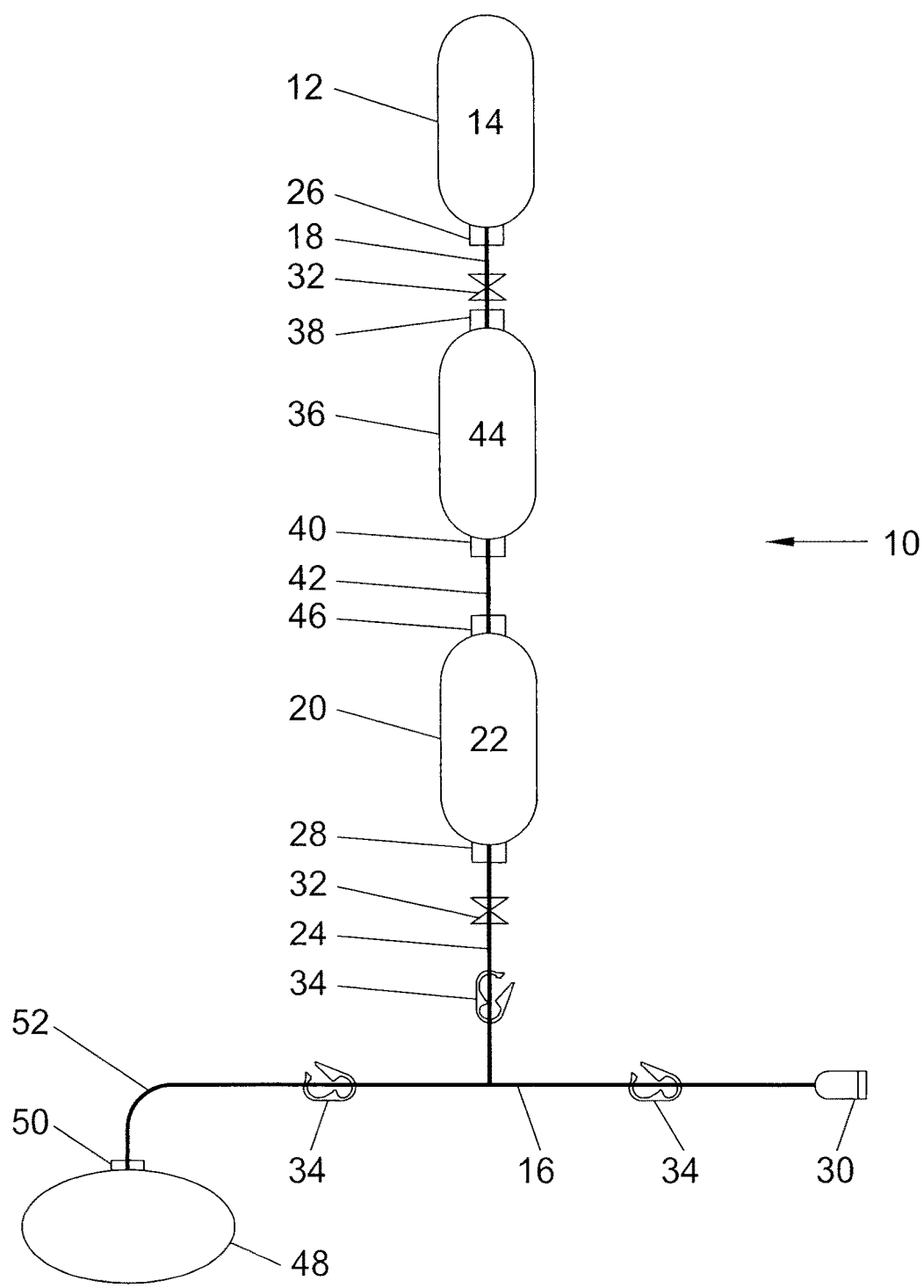
FIG. 2b illustrates another embodiment of the peritoneal dialysis set of the present invention showing three supply containers and a drain container, the third supply container positioned between, and in series with, the first and second supply containers.

FIG. 2b illustrates another embodiment of the peritoneal dialysis set of the present invention wherein a third supply container 36 is arranged between, and in series with, the first and second supply containers 12 and 20, respectively such that the first supply container 12 is connected to the third supply container 36 via the first supply tube 18 and the third supply container 36 is connected to the second supply container 20 through port 46 via the third supply tube 42 and the second supply container 20 is connected to the connecting tube 16 via the second supply tube 24. Third supply container 36 may contain at least one component 44 of the final dialysate that is the same as, similar to or different from, than the at least one component 14 and 22 of the first and second supply containers 12 and 20, respectively. In this embodiment, the peritoneal dialysis set 10 also contains a drain container 48 connected to the connecting tube 16 through port 50 via a drain tube 52. In this embodiment, the first and second supply tubes 18 and 24, respectively carry check valves 32, and second supply tube 24, connecting tube 16 and drain tube 52 carry clamps 34.

Figure 2C:
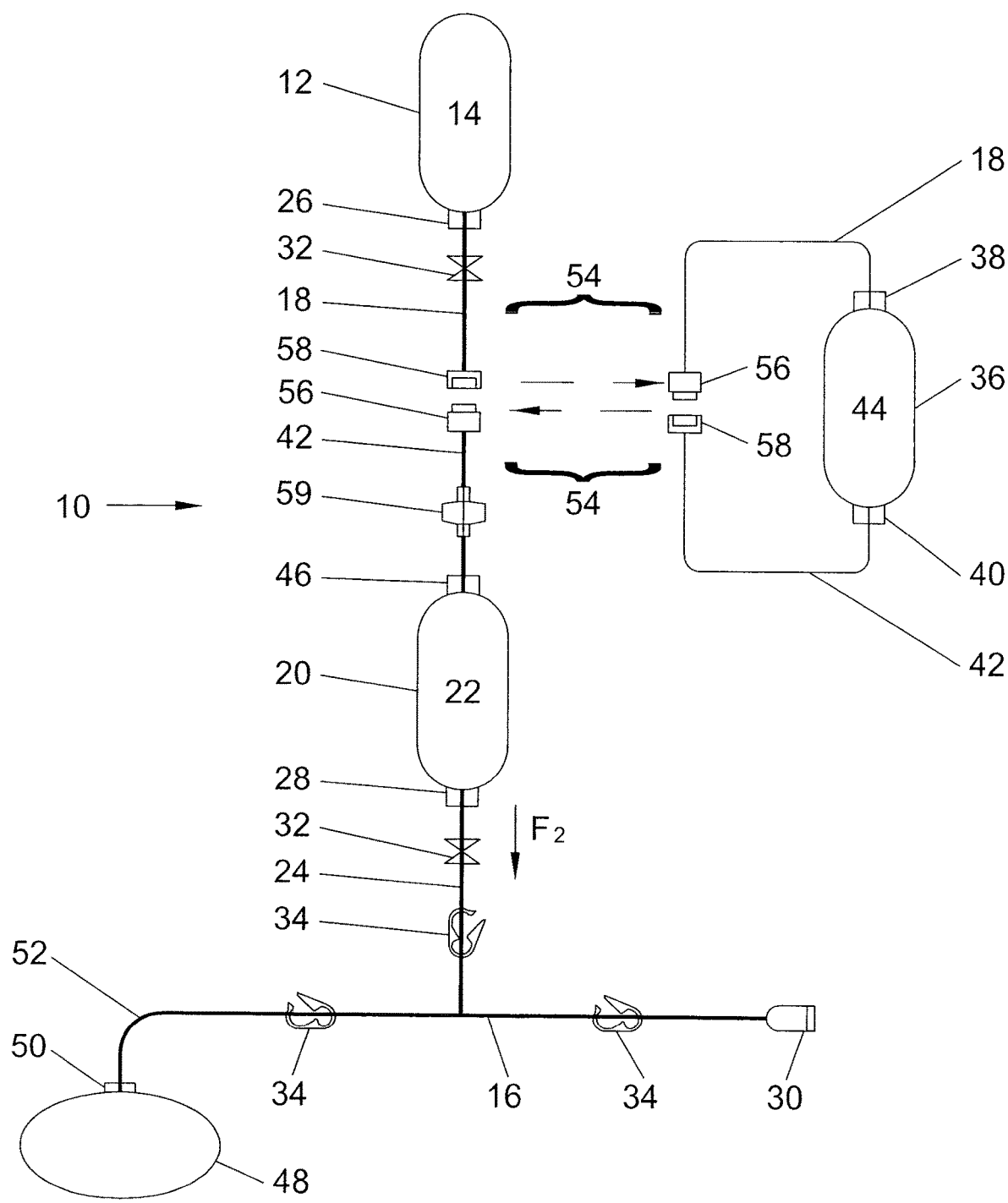
FIG. 2c illustrates an alternative embodiment of the peritoneal dialysis set illustrated in FIG. 2b wherein the third supply container is detachable.

FIG. 2c illustrates an alternative embodiment of the peritoneal dialysis set 10 illustrated in FIG. 2b wherein the third supply container 44 is readily attachable/detachable. In particular, the first and third supply tubes 18 and 42, respectively carry a locking connector 54 comprised of male and female engaging portions 56 and 58, respectively. In this embodiment, the third supply tube 42 carries a filter 59 between male engaging portion 56 of the locking connector 54 and port 46 of the second supply container 20.

Figure 3:
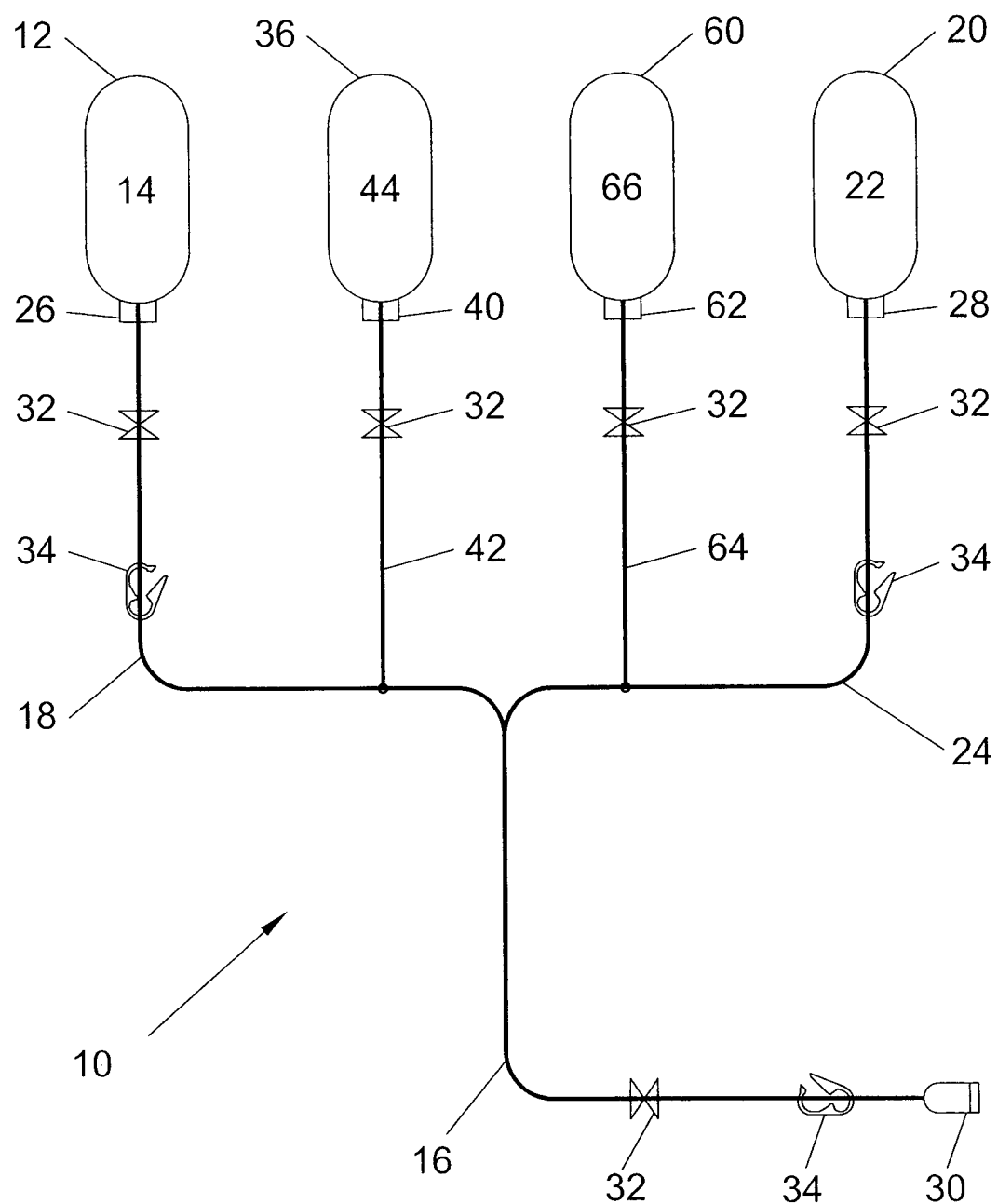
FIG. 3 illustrates another embodiment of the peritoneal dialysis set of the present invention showing four supply containers arranged in parallel, the third supply container connected to the first supply tube via a third supply tube and the fourth supply container connected to the second supply tube via the fourth supply tube.

FIG. 3 illustrates another embodiment of the peritoneal dialysis set 10 of the present invention with additional third and fourth supply containers 36 and 60, respectively, arranged in parallel with first and second supply containers 12 and 20, respectively. Third supply container 36 is connected to the first supply tube 18 via the third supply tube 42 and fourth supply container 60 is connected to the second supply tube 24 through port 62 via the fourth supply tube 64. Each of third and fourth supply containers 36 and 60, respectively, may be empty or may contain the same, similar or different components and/or volumes contained in first and second supply containers B1 and B2, respectively. In this embodiment, third and fourth supply containers 36 and 60, respectively contain a component 44 and 66, respectively of the final dialysate.

Figure 4A:
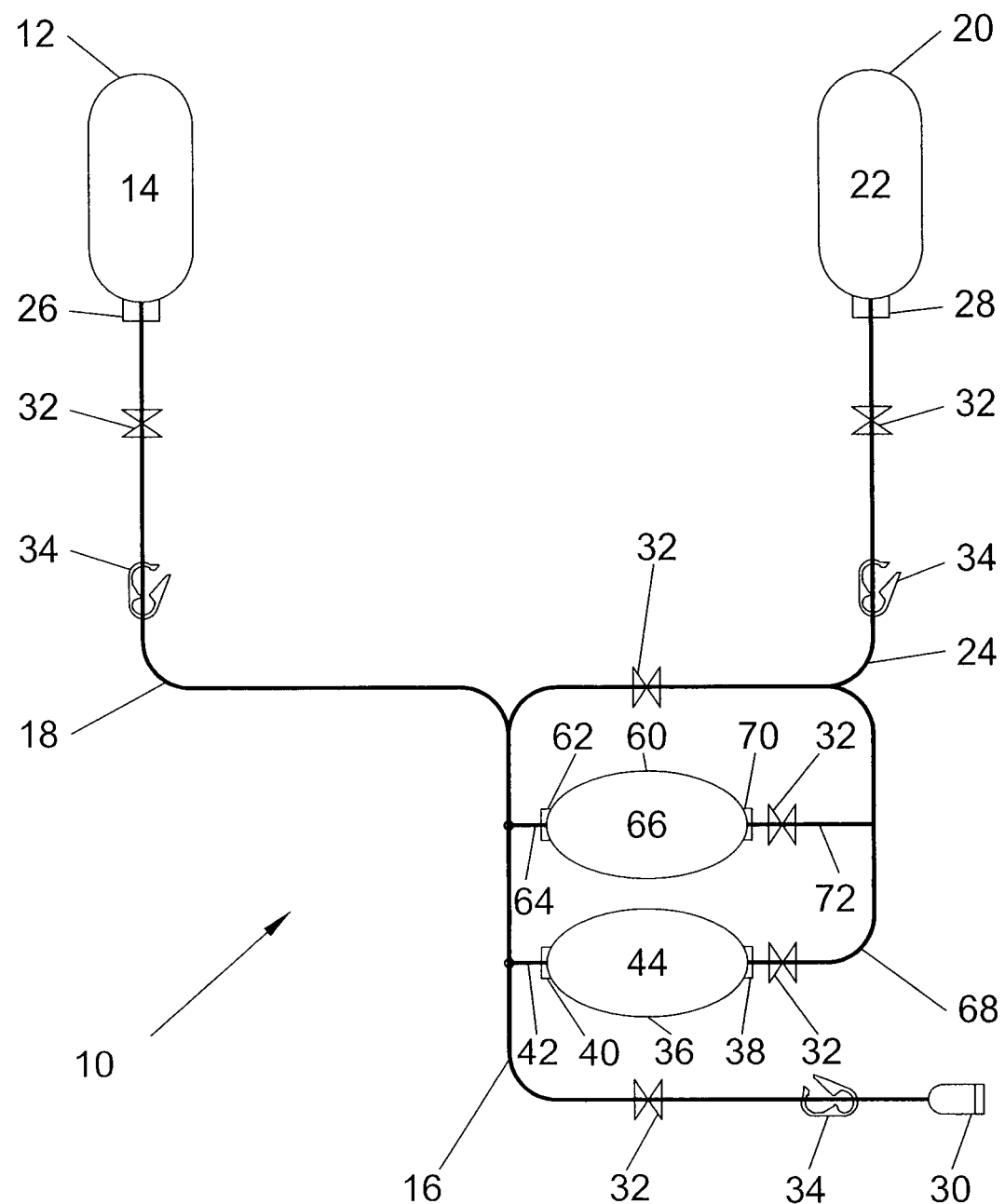
FIG. 4a illustrates another embodiment of the peritoneal dialysis set of the present invention showing four supply containers wherein the third and fourth supply containers are located in the common tubing of the main system.

FIG. 4a is an alternative embodiment of the peritoneal dialysis set 10 illustrated in FIG. 3 carrying third and fourth supply containers 36 and 40 arranged in parallel with the first supply container 12 and simultaneously arranged in parallel and in series with the second supply container 20. In particular, the third supply container 36 is connected to the second supply tube 24 through port 38 via a first input supply tube 68 and to the connecting tube 16 through port 40 via third supply tube 42. The fourth supply container 60 is connected to the first input supply tube 68 through port 70 via a second input supply tube 72 and to the connecting tube 16 through port 62 via fourth supply tube 64. In this embodiment, the first and second input supply tubes 68 and 72, respectively, carry check valves 32 and the second supply tube 24 carries a second check valve 32 located between the connection with the connecting tube 16 and the connection with the first input supply tube 68. The media 22 of the second supply container 20 may be circulated through the third supply container 36 or the fourth supply container 60 independently, or through both the third and fourth supply containers 36 and 60, respectively together, to produce a desired mixed product. Although not shown here, some of the tubing lines may have dual channels to facilitate re-circulation or bi-directional flow accordingly.

Figure 4B:
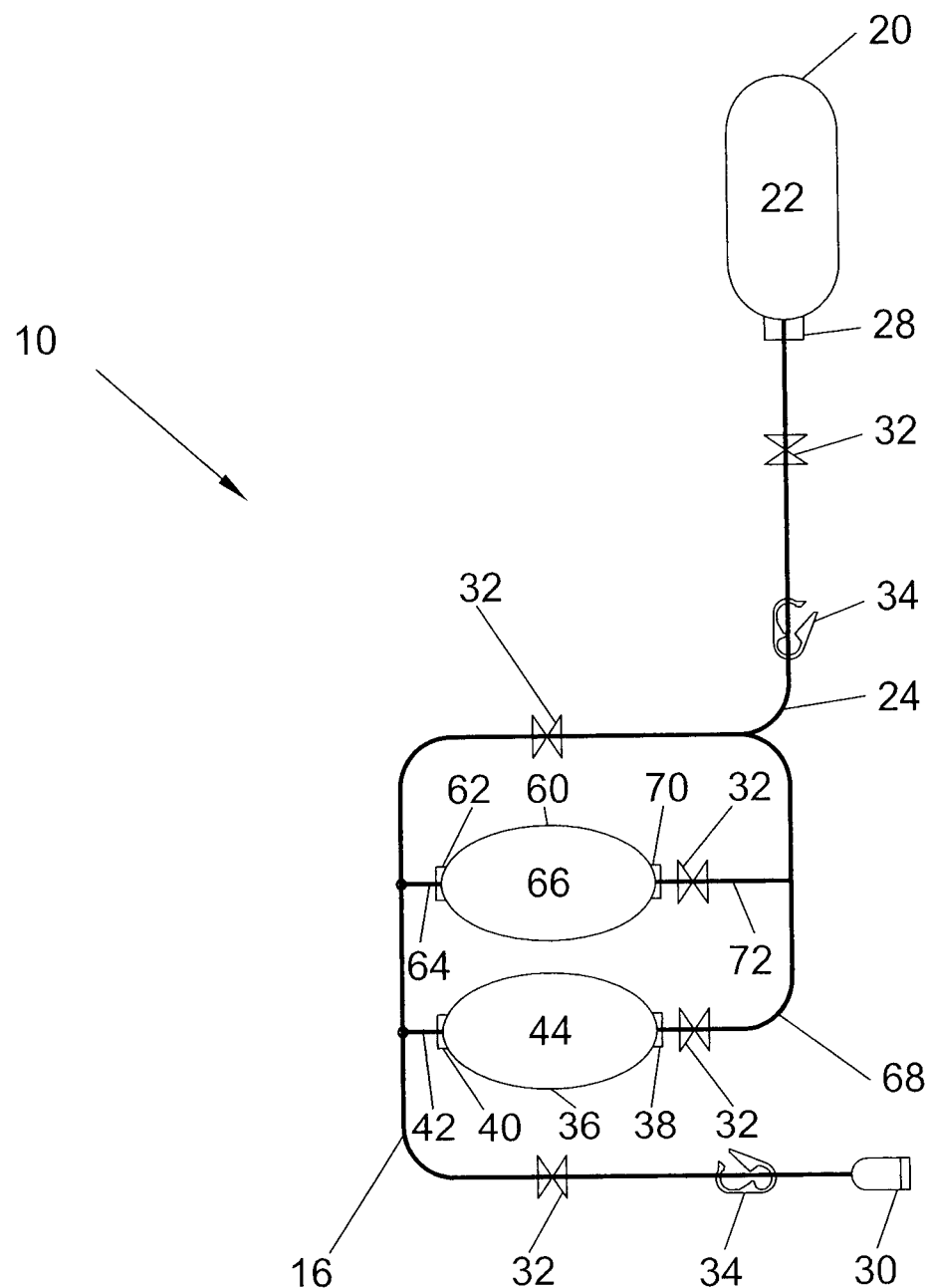
FIG. 4b is an alternative embodiment of the peritoneal dialysis set of FIG. 4, wherein the first supply container has been eliminated.

FIG. 4b is an alternative embodiment of the peritoneal dialysis set 10 illustrated in FIG. 4a wherein the first supply container 12 and its associated components have been eliminated.

The illustrations shown in FIG. 5a, FIG. 5b, FIG. 6a, FIG. 6b, FIG. 7, FIG. 8 and FIG. 9 teach alternate embodiments whereby some containers may not be attached to the main system from the beginning. They also give the flexibility for selecting alternate media and/or additives to be used at any time. A typical application is providing a safe, a reliable and a needle-less apparatus for adding medications into saline bags for IV infusion. The third supply container 36 or similar can be in the form of a syringe, and/or an infusion pump etc. The third supply container 36 may contain a medium produced at different time and/or at a different place, and be connected to the main apparatus via a locking connector 54, whenever required for modification and/or for completion of the desired product.

Figure 5A:
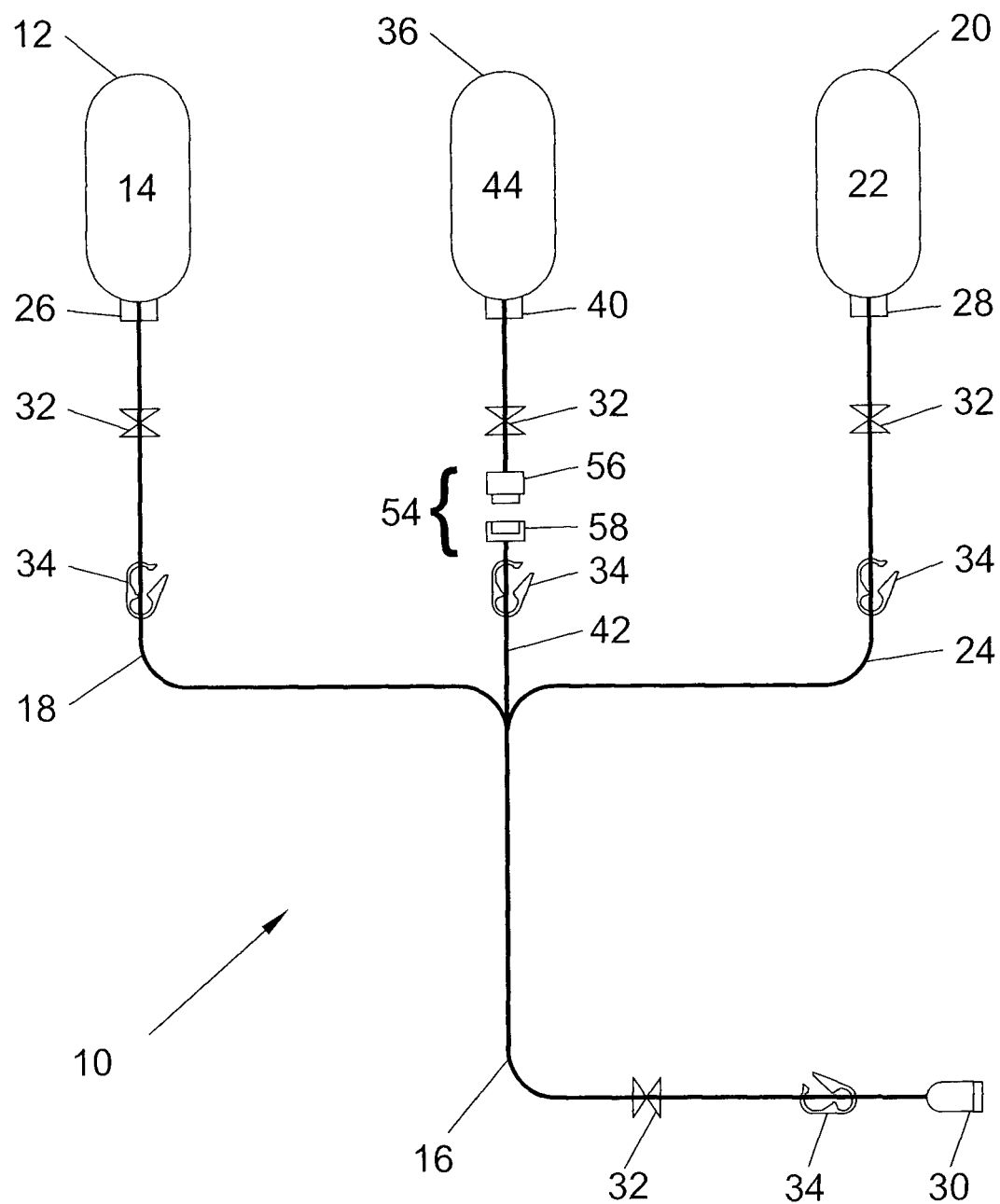
FIG. 5a illustrates an alternative embodiment of the peritoneal dialysis set illustrated in FIG. 2a wherein third supply container is an optional detachable container that when added to the set, is arranged in parallel with the first and second supply containers and is connected to the connecting tube via a third supply tube.

FIG. 5a illustrates an alternative embodiment of the peritoneal dialysis set 10 illustrated in FIG. 2a wherein the third supply container 36 is an optional detachable container that may be added later onto the system via a locking connector 54. The third supply container 36 may not be attached to the main system to start with and may not even be connected to the system at all. If and when the third supply container 36 is attached to the system, it is arranged in parallel with first and second supply containers 12 and 20, respectively. In this embodiment, supply container 36 is detachable at locking connector 54.

Figure 5B:
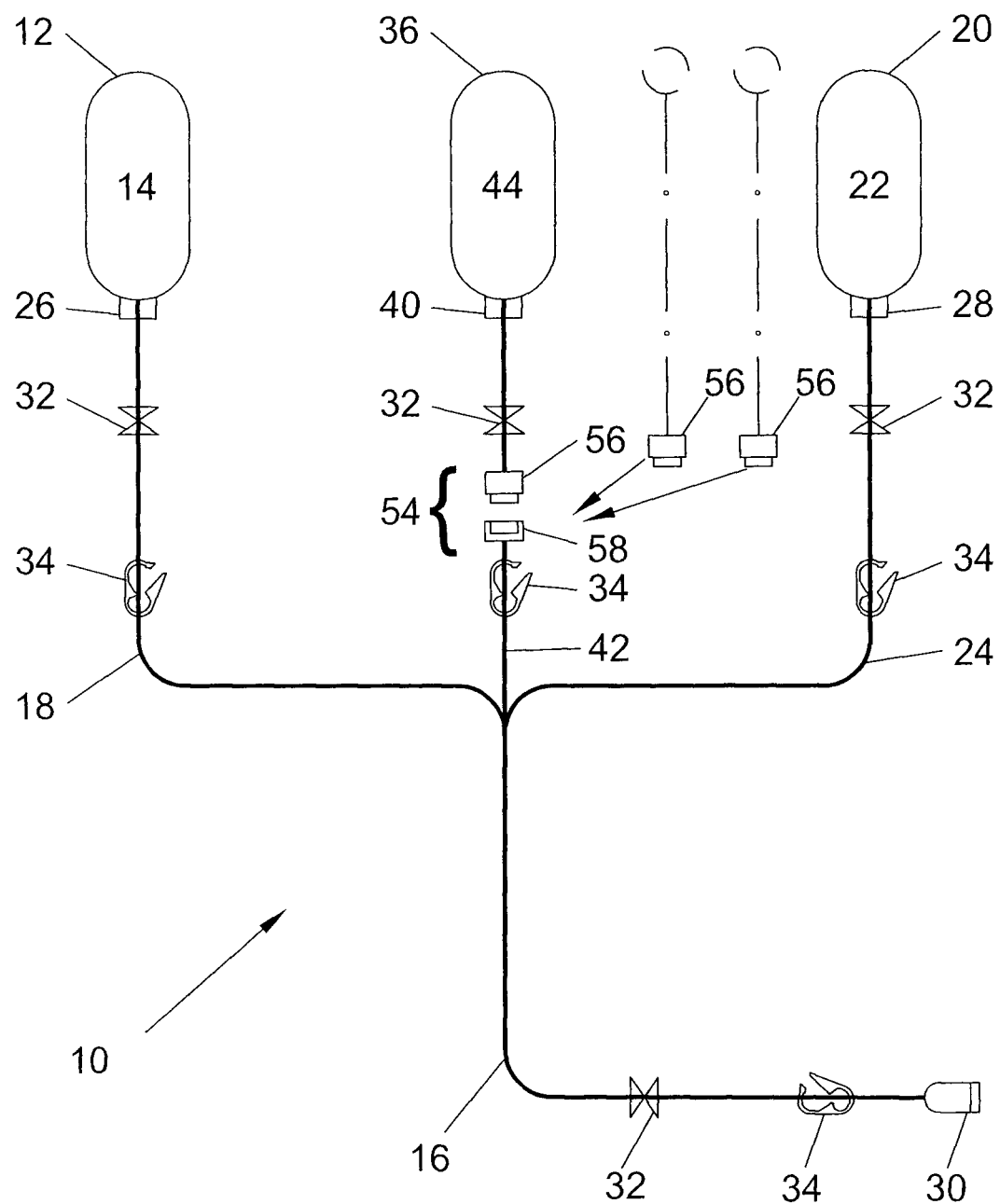
FIG. 5b illustrates the embodiment of the peritoneal dialysis set of FIG. 5a wherein multiple third supply containers may be added to, and removed from, the set one after another.

FIG. 5b illustrates an alternative embodiment of the multi-container system apparatus 10 illustrated in FIG. 5a employing multiple detachable third supply containers 36 that may be coupled to the female engaging portion 58 of the locking connector 54, one at a time, one after another, to extend the application of the system. No micron filter is shown here. But for such a system, placement of a filter between the locking connector 54 and clamp 34 is highly recommended. In this embodiment, first supply container 12 may be empty or not. However, first supply container 12, may also double up as a drain container if necessary. It is also possible for those schooled in the art to produce variations of the arrangements demonstrated above. The containers may also be arranged and used in sequential order of preferred steps of combining/mixing of the required media.

Some of the media may be gases, solids, powders, crystals, granular and/or salts etc., so packaged in the dry states, to avoid growth of bacteria. If this were the case, then to produce the desired resultant media, fluid may first be directed to flow from liquid containing containers into the container(s) storing the dry media, to dissolve such said dry media accordingly. It is also possible that under certain favorable arrangements the reverse procedure may be possible.

Figure 6A:
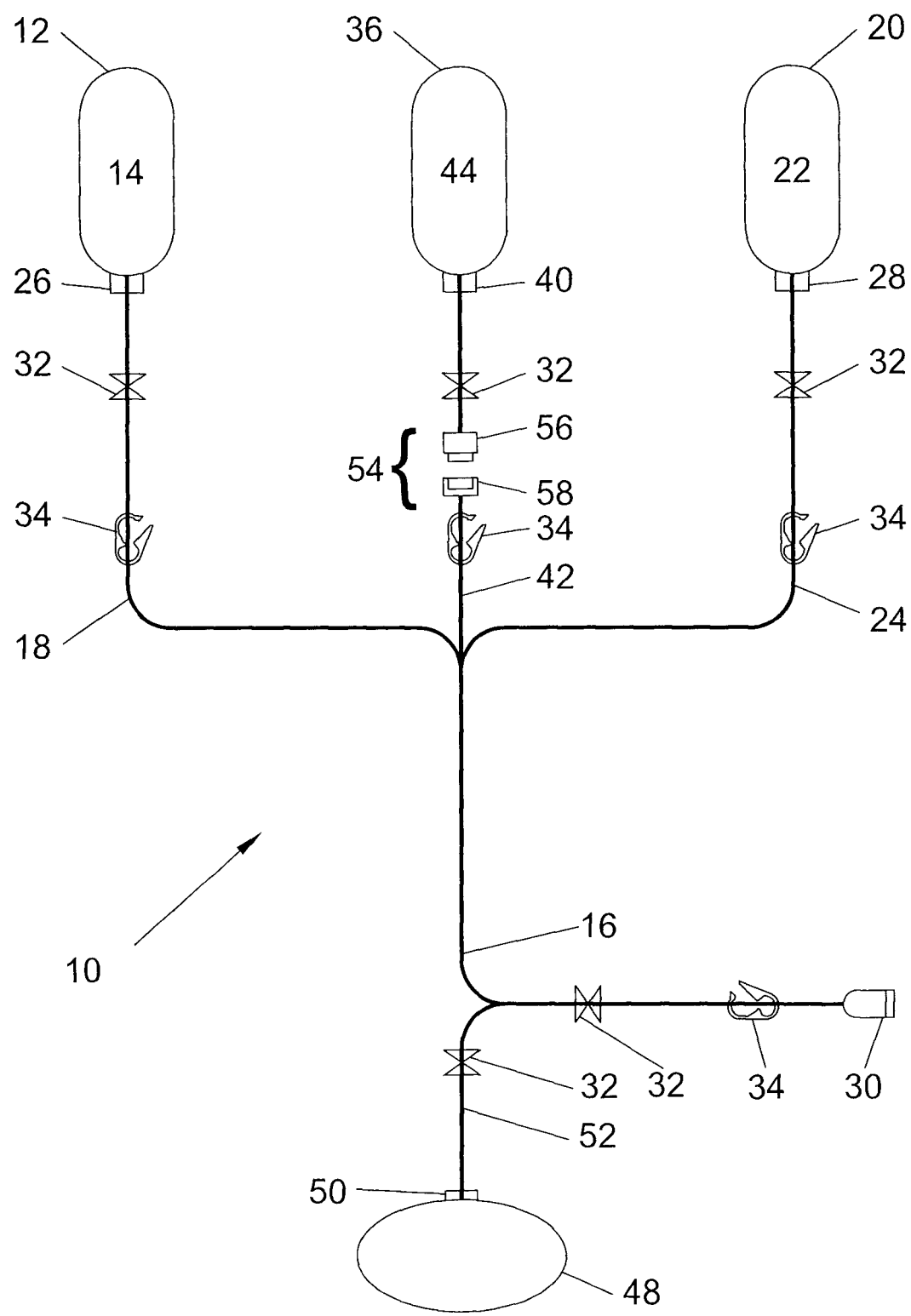
FIG. 6a illustrates an alternative embodiment of the peritoneal dialysis set illustrated in FIG. 5a showing a drain container connected to the connecting tube via a drain tube.

FIG. 6a illustrates an alternative embodiment of the multi-container system apparatus 10 illustrated in FIG. 5a wherein a drain container 48 is attached to the connecting tube 16 and is employed to accommodate partial flushing of any container, that is originally attached and/or to be attached later. The addition of drain container 48, gives the flexibility for the patient to start draining his/her used dialysate into drain container 48 whilst the contents of the first, second and third supply containers 12, 20 and 36, respectively are being mixed together as explained above. In this embodiment, the drain tube 52 carries a check valve 32.

Figure 6B:
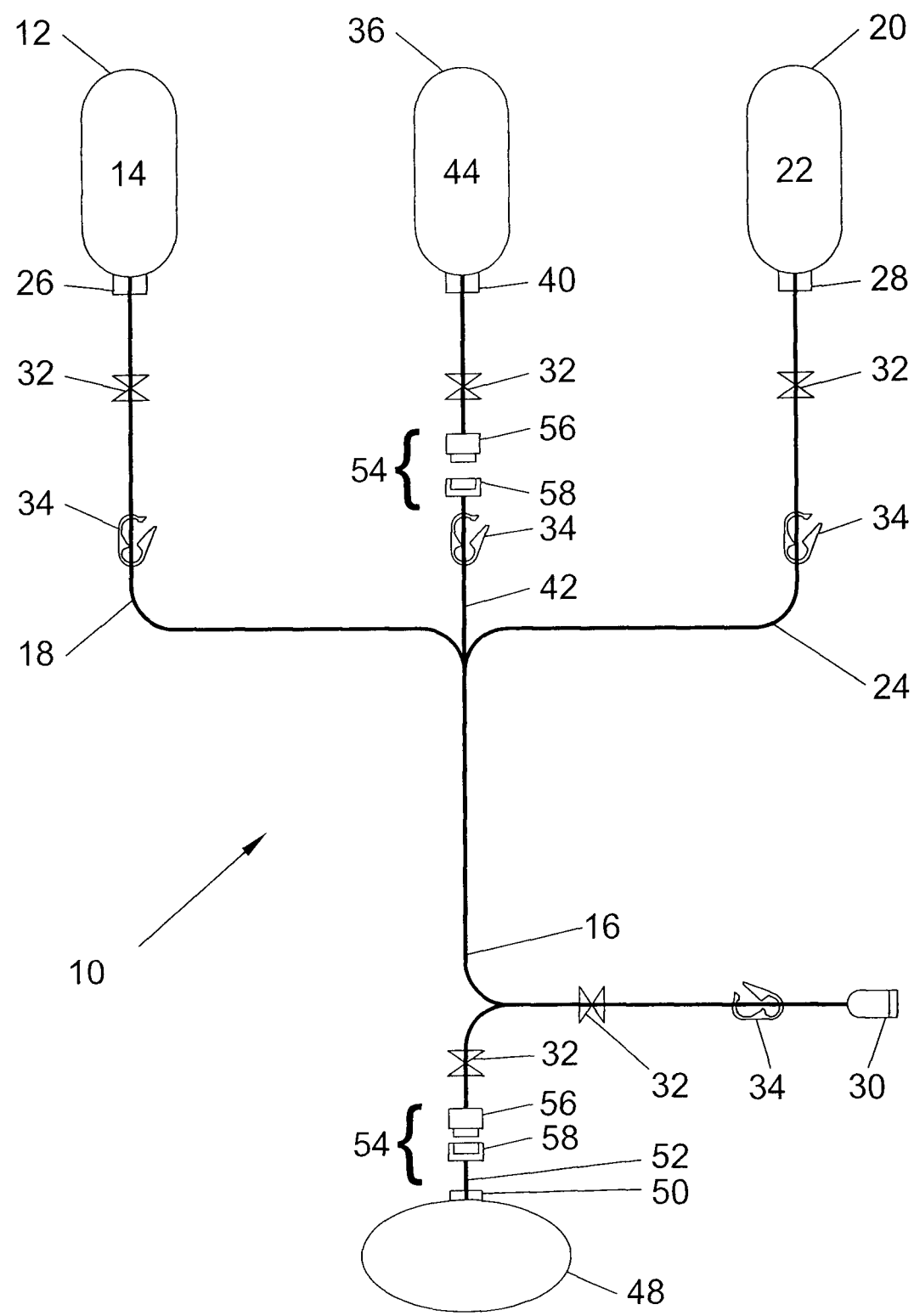
FIG. 6b illustrates an alternative embodiment of the peritoneal dialysis set illustrated in FIG. 6a wherein the drain container is detachable.

FIG. 6b illustrates an alternative embodiment of the multi-container system apparatus 10 illustrated in FIG. 6a wherein there is an alternate attachment for drain container 48 in the form of a locking connector 54 in the drain tube 52 leading to drain container 48. This allows drain container 48 to be used as either a drain and/or a sampling container. The locking connector 54 makes it possible for drain container 48 to be added to the system 10 at a later time. It also allows the flexibility for collecting samples of media through the locking connector 54. It is possible to first couple the third supply container 36 to the locking connector 54 in the third supply tube 42, empty its contents 44 then relocate the third supply container 36 at the locking connector 54 in the drain tube 52 and use the third supply container 36 as a drain container 48. This would eliminate the use of the additional drain container 48. Again, the flexibility of this invention makes it possible for any arrangement shown from FIGS. 1 to 9, to employ drain container 48 accordingly.

Figure 7:
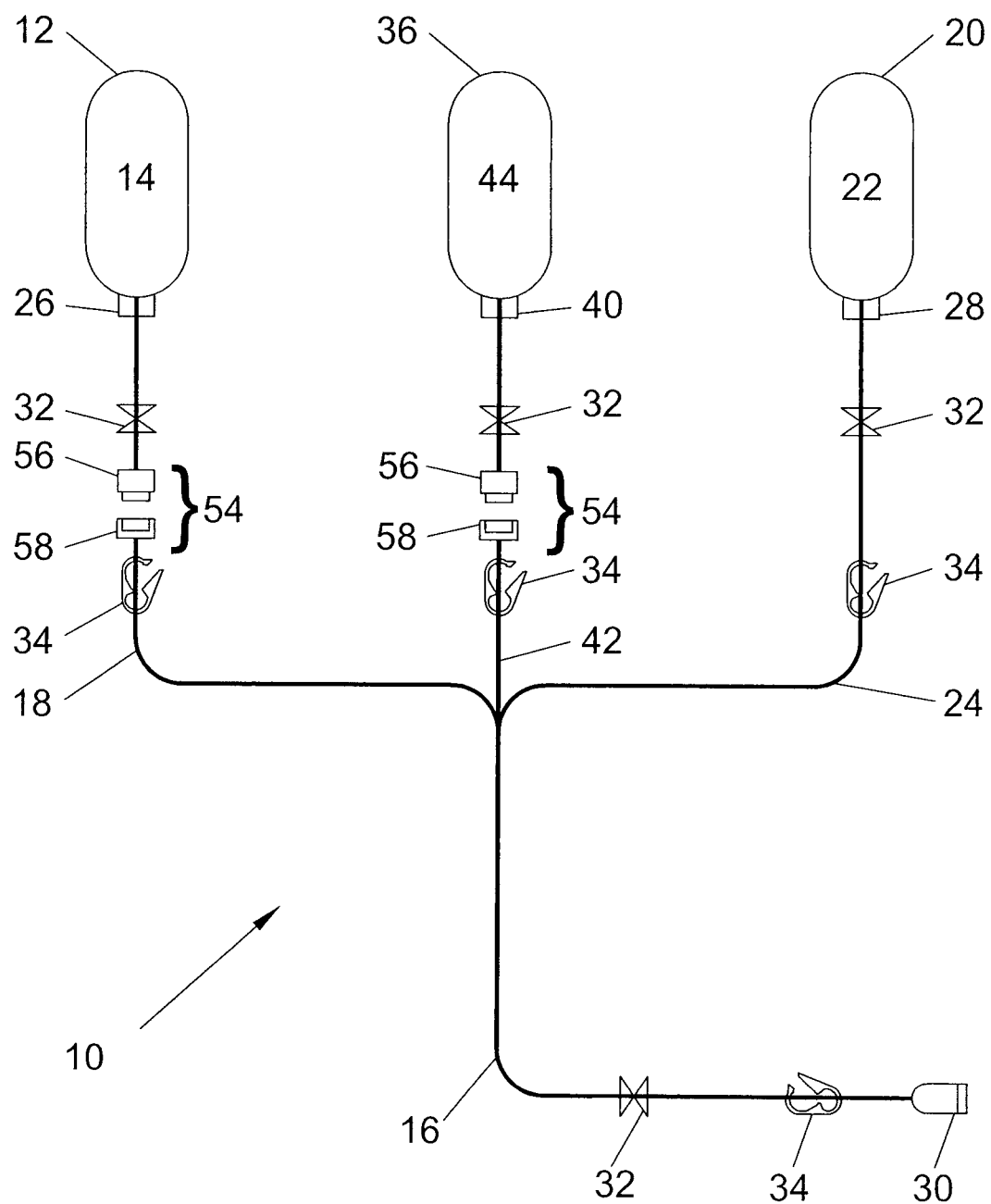
FIG. 7 illustrates an alternative embodiment of the peritoneal dialysis set illustrated in FIG. 5a wherein the first supply container is also detachable.

FIG. 7 is another alternate embodiment of FIG. 5 already discussed above. This illustration shows the two additives, 14 and 44, contained in optional first and third supply containers 12 and 36, respectively, to be added now and/or later, or may be entirely omitted. The locking connectors 54 of the first and third supply tubes 18 and 42, respectively may accommodate unlimited multiple containers. This embodiment also allows either first supply container 12 or third supply container 36 to be used later as drain and/or sample container.

Figure 8:
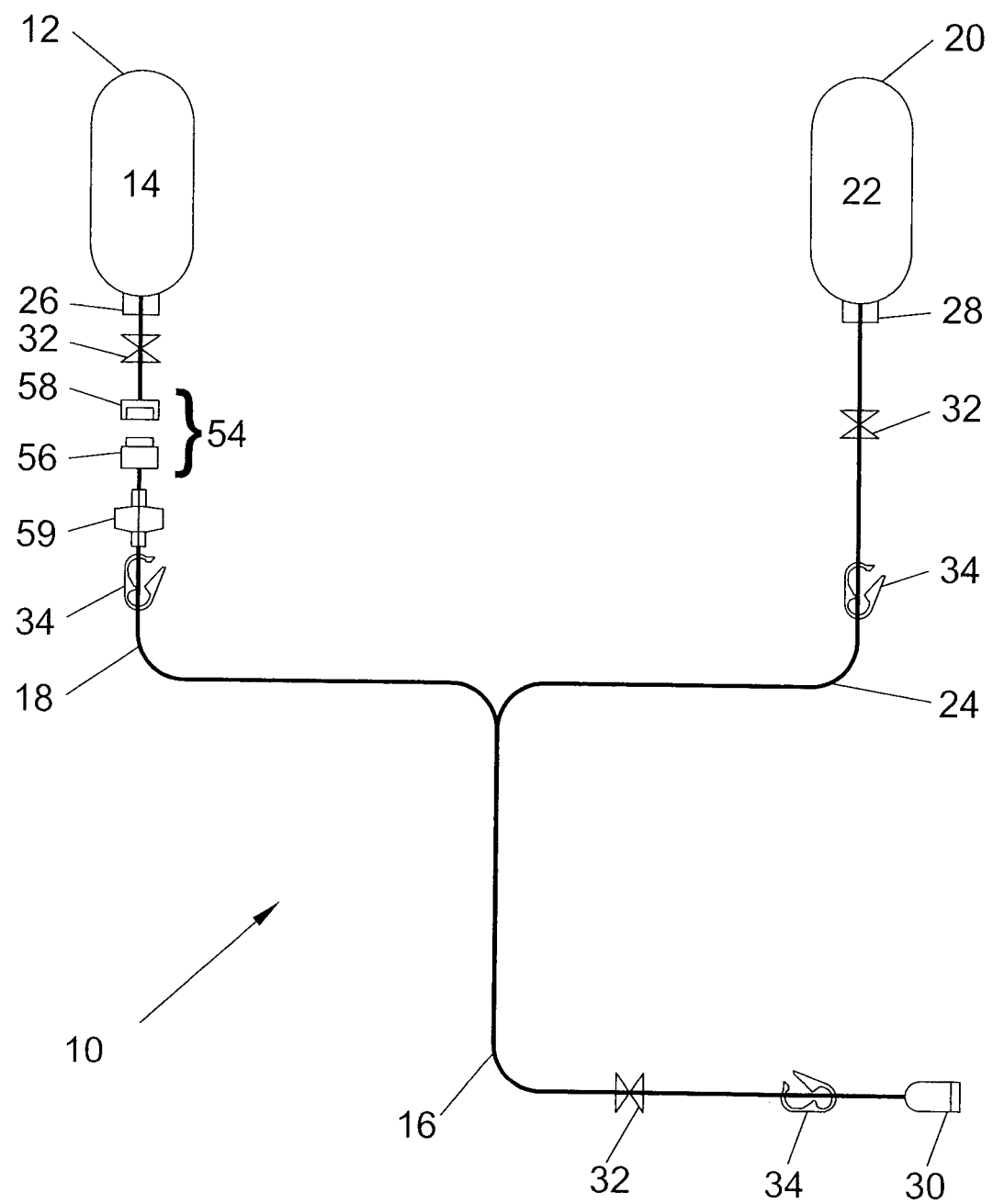
FIG. 8 illustrates an alternative embodiment of the peritoneal dialysis set illustrated in FIG. 1a wherein the first supply container is detachable.

FIG. 8 illustrates an alternate embodiment of the apparatus 10 illustrated in FIG. 1. In FIG. 8 the first supply container 12 is detachable from the apparatus 10 via locking connector 54 carried by first supply tube 18. First supply tube 18 carries a filter 59 between the locking connector 54 and the clamp 34. In this embodiment, first supply container 12 is detachable from the apparatus 10 and may double up as a drain and/or sample container. The filter H1, in one embodiment, may be a Micron Filter HP.

Figure 9:
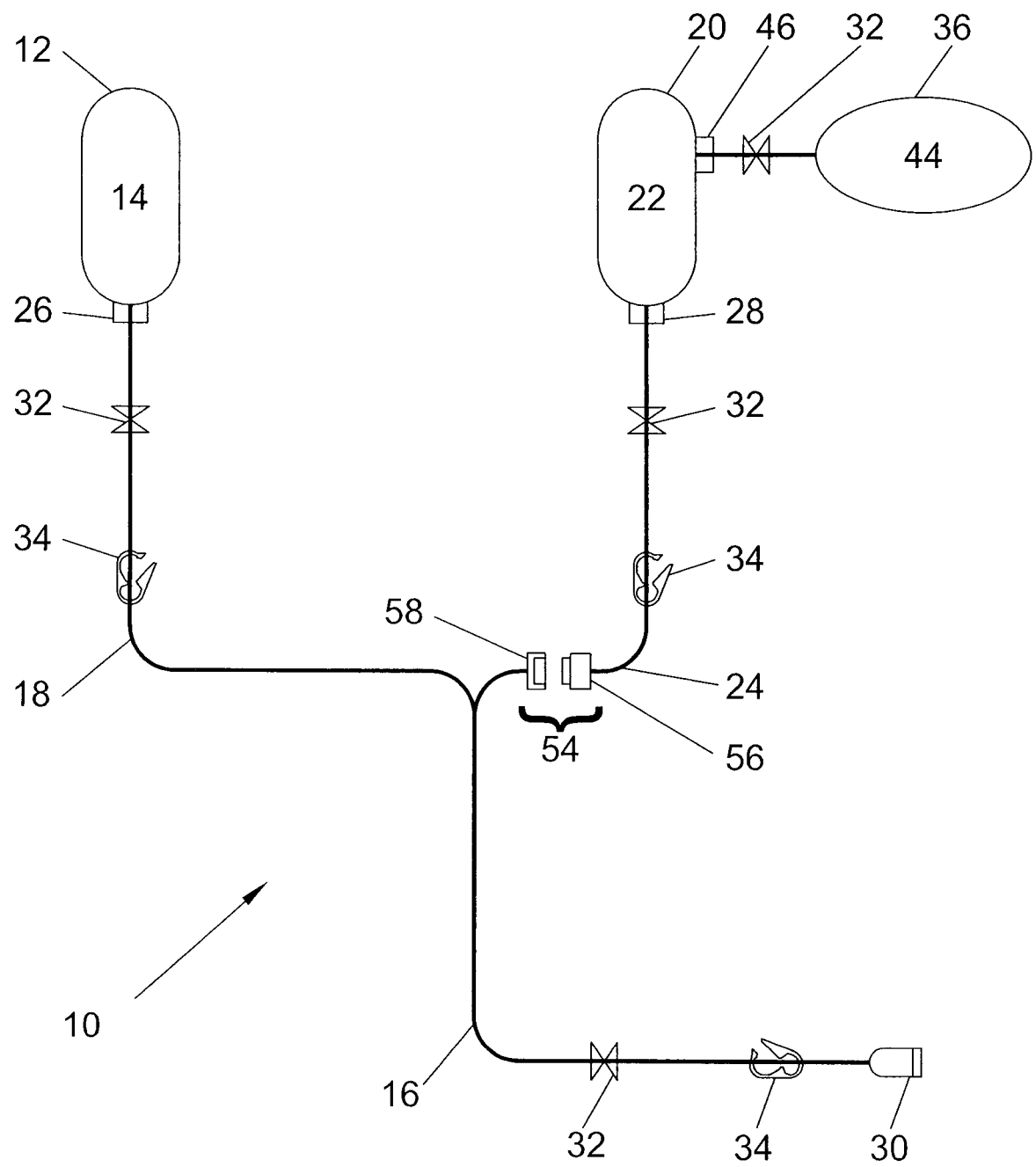
FIG. 9 illustrates an alternative embodiment of the peritoneal dialysis set illustrated in FIG. 1a wherein the second supply container is detachable and the set further comprises a third supply container arranged in series with second supply container.

FIG. 9 illustrates an alternate embodiment of the apparatus 10 illustrated in FIG. 2a. In FIG. 9, the third supply container 36 is connected to second supply container 20 via the third supply tube 42 and the second supply tube 24 of the second supply container 20 carries a locking connector 54 such that the second and third supply containers 20 and 32 respectively are detachable from the apparatus 10. The second and third supply containers 20 and 36 could form multiple sub-sets of different component combinations and/or additives that could be added onto the apparatus 10 at the time of application.

All or some of the containers, especially the detachable ones, may bear markers and/or graduations at their sides that may be used to discharge in whole or in part, or ratios of their contents, to generate required overall desired product and/or formulations.

The embodiments of the present invention, one of which is as shown in FIG. 1 and all the alternatives as described above and/or implied, could equally be fitted with similar storage/drain containers, detachable coupling connectors, and/or micron filters wherever applicable, desirable and/or needed. For example, a micron filter HP could be employed at every detachable connector.

For the purpose of illustration, the following examples are presented which should not be considered as limiting to the scope of the present invention.

EXAMPLES

Example #1

Peritoneal Dialysis

The demonstration of this application for peritoneal dialysis refers to the basic embodiment illustrated in FIG. 1a and its extensions FIG. 1b and FIG. 1c.

Step 1
  (i) Close all clamps
  (ii) Lower bag 12 to Level 3 (Ground Level)
  (iii) Open Clamp 34 on line 18
  (iv) Open Clamp 34 on line 24
  (v) Break to open valve 32 in line 18
  (vi) Break to open valve 32 in line 24
  (vii) Allow fluid from bag 20 to empty completely into bag 12
  (viii) Shake bag 12 to mix thoroughly the composite fluid (14+22) in bag 12
  (ix) Close Clamp 34 on line 18
Step 2
  (i) Move bag 12 to Level 1
  (ii) Move bag 20 to Level 3, below both Level 1 and Level 2 (patient's height)
Step 3
  (i) Connect Patient Line Connector 30 to the patient's Transfer set (not shown) or patient's line (not shown)

(ii) Open clamp on the patient's Transfer Set (not shown)
(iii) Open Clamp 34 on line 16
(iv) Break to open valve 32 in line 16
(v) Allow patient to drain waste dialysate (used dialysis fluid currently in the peritoneum) into bag 20 (serving as a Drain Bag)

Step 4: Flush-Before-Fill
(i) Close clamp 34 in line 16
(ii) Open Clamp 34 in line 18 for about 5 seconds to flush solution from bag 12 into bag 20
(iii) Close Clamp 32 on line 24

5: Filling Patient
(i) Open Clamps on Transfer Set (not shown here)
(ii) Open Clamp 34 on line 16
(iii) Allow dialysate (composite fluid) to flow from bag 12 into patient through Patient Line Connector 30

Step 6: Disconnecting Patient
(i) Close all clamps; Clamps (34) and, Clamp on Transfer Set (not shown).
(ii) Disconnect Patient Line Connector 30 from Transfer Set connector (not shown here).
(iii) Safely and quickly cap off the end of Transfer Set connector with Disinfectant Cap (not shown here)
(iv) Cap off Patient Line Connector 30
(v) Safely discard the Multi-Container System Set Example #2

Medicated Solution

This will demonstrate application for producing desirable medicated solution for medical treatment. For example, for administering medications (i.e., intravenous (i.v.)) and/or for providing feeding fluids for parenteral nutrition. These could be made possible using illustrations shown in FIGS. 5a, 5b, 6a, 6b, 7 and/or 8. Referring to the embodiment shown in FIG. 8 as a typical example, steps for producing safe medicated IV solutions are set out below. With this application a Micron Filter 59, although highly recommended, is optional.

Initial Step 1
(i) Close all clamps (34)
(ii) Check and select the prepared medication dosage stored in container 12.
(iii) Attach container 12 via locking connector 54 to the main set carrying the container with the appropriate base solution 22, (saline etc.)
(iv) Break to open valve 32 in line 18
(x) Open Clamp 34 on line 18
(xi) Break to open valve 32 in line 24
(xii) Open Clamp 34 on line 24
(xiii) Allow the correct amount of medication 14 to flow into container 20
(xiv) Close clamp 34 on line 18
(xv) Close clamp 34 on line 24
(xvi) Shake bag 20 to mix thoroughly the composite fluid (14+22) in bag 20

Step 2: Application
(i) Attach line connector 30 to IV line or to infusion pump (not shown here)
(ii) Break to open valve 32 in line 16
(iii) Open clamp 34 on line 16
(iv) Open clamp 34 on line 24
(v) Start the infusion therapy as per direction Step 3: Ending Therapy
(i) At the end of infusion, close clamp 34 on line 24
(ii) Close clamp 34 on line 16
(iii) Disconnect line connector 30 from the infusion pump or the IV line (not shown here)
(iv) Discard the set accordingly The illustration shown in FIG. 7 may be used for the process described above if two different medications are to be added to saline accordingly. Then container 36 may house the second medication 44. All the medications may be pre-filled and labeled accordingly by the pharmacists.

Example #3

Food Packaging, Preservation and/or Storage

A practical application for food packaging, preservation and/or storage and the final usage is demonstrate by the embodiment illustrated in FIG. 8.

Dehydrated food such as wheat, oats\*, baby food (may be in flour or granular format), corn flour, food for soldiers (to be carried and used during field combats), and special formulated food for astronauts etc., may be packaged under vacuum in container 20. [It makes it easier for long-term preservation. In dehydrated form, these packages are also very lightweight for transporting around]. The packaged system may be sterilized accordingly if so desired.

Step 1: Connections.
(i) Close all clamps (34)
(ii) Take the appropriate container 12 housing the desired fluid: Water, milk, soup, etc., (may be heated before use)
(iii) Remove the covers off the locking connector 56 & 58
(iv) Attach 12 to the appropriate system using locking connector 54
(v) Break to open valve 32 attached to output 26
(vi) Open clamp 34 of line 18
(vii) Open clamp 34 of line 24
(viii) Break to open valve 32 in line 24
(ix) Transfer the fluid 14 from container 12 through the Micron Filter 59\*\* into container 20 by applying pressure to container 12, or by lowering container 20 below container 12
(x) Close clamp 34 in line 24
(xi) Give required time for the food in 20 to hydrate properly.
(xii) The final food could be warmed or heated up before consumption if so desired.

NOTE:—\* These food products may be grated and roasted to produce hydrated granular or flour, that could be preserved for months. They may be sealed under vacuum.

\*\* The Micron Filter 59 may be essential to purify water and/or fluid that may be suspect of contaminations as the case may be, in the developing World or in certain uncontrolled locations such as campgrounds, wildlife, recreational areas and/or battlefields.

Example #4

Mixing Paint Colours

The present invention may be applied for mixing paints using embodiment shown in FIG. 7. Here, variations of extended embodiments illustrated in FIG. 3 and FIG. 7 may be used to demonstrate practical applications for mixing paint colors.

Sighting FIG. 7 for this demonstration, container 20 may contain the basic white paint or the desired base color. Two additional colors may be housed in containers 12 and 36.

Step 1: Connections
  (i) Close all clamps (34)
  (ii) Select the main system that contains the base color in 20.
  (iii) Select containers 12 and 36 housing the colors to be added in ratio. (These containers will have appropriate graduations on them).
  (iv) Remove the covers from their respective connectors
  (v) Attach container 12 to the system via locking connector 54 in line 18
  (vi) Attach container 36 to the system via locking connector 54 in line 42
Step 2: Adding the First Color
  (i) Break open valve 32 of container 12
  (ii) Open clamp 34 on line 18
  (iii) Break open valve 32 in line 24
  (iv) Apply pressure to container 12 or raise it high above container 20
  (v) Open clamp 34 on line 24
  (vi) Allow the correct amount of additive paint 14 to flow into container 22
  (vii) Close clamp 34 on line 18
  (viii) Close clamp 34 on line 24
Step 3: Adding the Second Color
  (i) Break open valve 32 of container 36
  (ii) Open clamp 34 on line 42
  (iii) Apply pressure to container 36 or raise it high above container 20
  (iv) Open clamp 34 on line 24
  (ix) Allow the correct amount of additive paint 44 to flow into container 22
  (v) Close clamp 34 on line 42
  (vi) Close clamp 34 on line 24
  (vii) Shake container 20 thoroughly to obtain the desired color
  (viii) The paint may be discharged for use through line connector 30.

Note: Alternate or different color additives may be housed in alternate containers to 12 and 36 etc. and could be added via either locking connectors 54 respectively following the same procedure stated above.

Any one of the embodiments of this invention, the Multi-Container System, may be operated manually or with an assistance of a device, equipment and/or a machine.

While the foregoing provides a detailed description of preferred embodiments of the present invention, it is to be understood that it is intended that all material contained herein be interpreted as illustrative of the present invention only and not in a limiting sense. Furthermore, numerous modifications, variations and adaptations may be made to the particular embodiments of the present invention described above without departing from the scope of the present invention, which is defined in the claims.

The embodiments of the invention in which an exclusive property or privilege is claimed are as follows:

1. A peritoneal dialysis method comprising:
  connecting at least two independent supply containers to a connector, each independent supply container of the at least two independent supply containers containing at least one component of a final dialysate for filling a patient, a first independent supply container of the at least two independent supply containers containing at least a first component of the final dialysate, and a second independent supply container of the at least two independent supply containers containing at least a second component of the final dialysate, wherein the contents of the first independent supply container are in a solid or a semi-solid form and the contents of the second independent supply container are in a liquid form;
  transferring at least a portion of the contents of the second independent supply container to the first independent supply container, wherein, prior to transferring at least a portion of the contents of the second independent supply container to the first independent supply container, the first independent supply container contains the first component but does not contain the second component, and the second independent supply container contains the second component but does not contain the first component;
  mixing the at least a portion of the contents of the second independent supply container with the contents of the first independent supply container to form at least a portion of the final dialysate;
  connecting the connector to a transfer set of the patient;
  draining a used dialysate from the patient through the connector into the second independent supply container; and
  filling the patient from at least the first independent supply container to perform a dialysate dwell.

2. The peritoneal dialysis method of claim 1, wherein the transfer of the at least a portion of the contents of the second independent supply container to the first independent supply container is a partial transfer of the contents of the second independent supply container to the first independent supply container.

3. The peritoneal dialysis method of claim 1, wherein the transfer of the at least a portion of the contents of the second independent supply container to the first independent supply container is a complete transfer of the contents of the second independent supply container to the first independent supply container.

4. The peritoneal dialysis method of claim 1, wherein connecting the at least two independent supply containers to the connector comprises connecting a supply tube of each of the at least two independent supply containers to a connecting tube connected to the connector.

5. The peritoneal dialysis method of claim 1, wherein connecting the connector to the transfer set of the patient includes at least one of: (i) providing a cap on the connector that is removed for connection; and (ii) configuring the connector to be fluidly connected to the transfer set of the patient.

6. The peritoneal dialysis method of claim 1, wherein draining the used dialysate of a previous dwell from the patient through the connector comprises preventing flow from the at least two independent supply containers to the connector, preventing flow from the first independent supply container to the second independent supply container, and urging flow from the patient to the second independent supply container.

7. The peritoneal dialysis method of claim 6, wherein urging flow from the patient to the second independent supply container comprises lowering the second independent supply container below the transfer set of the patient.

8. The peritoneal dialysis method of claim 1, wherein filling the patient from the first independent supply container comprises preventing flow from the connector to the second independent supply container, preventing flow from the first independent supply container to the second independent supply container, and urging flow from the first independent supply container through the connector to the patient.

9. The peritoneal dialysis method of claim 8, wherein urging flow from the first independent supply container through the connector to the patient comprises raising the first independent supply container above the transfer set of the patient.

10. The peritoneal dialysis method of claim 1, wherein transferring the at least a portion of the second independent supply container to the first independent supply container comprises preventing flow from the second independent supply container to the connector and urging flow from the second independent supply container to the first independent supply container.

11. The peritoneal dialysis method of claim 10, wherein urging flow from the second independent supply container to the first independent supply container comprises lowering the first independent supply container below the second independent supply container.

12. The peritoneal dialysis method of claim 1, further comprising flushing a connecting tube connected to the connector and a supply tube of each of the first independent supply container and the second independent supply container by preventing flow from the second independent supply container to the first independent supply container and urging flow from the first independent supply container through the supply tube of the first independent supply container, the connecting tube and the supply tube of the second independent supply container and into the second independent supply container.

13. The peritoneal dialysis method of claim 1, further comprising allowing for a dialysate dwell by preventing flow from the at least two independent supply containers to the connector and by preventing flow through the connector.

14. The peritoneal dialysis method of claim 1, further comprising disconnecting the transfer set transfer set of the patient from the connector during the dialysate dwell.

15. The peritoneal dialysis method of claim 1, wherein prior to filling the patient from at least the first independent supply container, the first independent supply container contains the final dialysate and wherein filling the patient from at least the first independent supply container comprises filling the patient from only the first independent supply container with the final dialysate to perform the dialysate dwell.

16. The peritoneal dialysis method of claim 1, wherein when the at least first component is an osmotic agent, the at least second component is a buffering agent or when the at least first component is a buffering agent, the at least second component is an osmotic agent.

17. The peritoneal dialysis method of claim 16, wherein the osmotic agent has a pH that is lower than the pH of the final dialysate.

18. The peritoneal dialysis method of claim 16, wherein the concentration of the osmotic agent in the final dialysate is selected from the group consisting of 1.5%, 2.5% and 4.25%.

19. The peritoneal dialysis method of claim 16, wherein the osmotic agent is selected from the group consisting of glucose, dextrose, amino acids, icodextrin and combinations thereof.

20. The peritoneal dialysis method of claim 16, wherein the buffering agent is selected from the group consisting of a bicarbonate, a lactate and combinations thereof.

21. The peritoneal dialysis method of claim 16, wherein the first independent supply container and/or the second independent supply container contains an electrolyte.

22. The peritoneal dialysis method of claim 21, wherein the electrolyte is selected from the group consisting of calcium, sodium, potassium, chloride and combinations thereof.

* * * * *